US006673364B1

(12) United States Patent
Holland et al.

(10) Patent No.: US 6,673,364 B1
(45) Date of Patent: Jan. 6, 2004

(54) LIPOSOME HAVING AN EXCHANGEABLE COMPONENT

(75) Inventors: John W. Holland, Glebe (AU); Thomas D. Madden, Vancouver (CA); Pieter R. Cullis, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/094,540

(22) Filed: Jun. 12, 1998

Related U.S. Application Data

(63) Continuation of application No. 08/485,608, filed on Jun. 7, 1995, now Pat. No. 5,885,613.

(51) Int. Cl.[7] .............................................. A61K 9/127
(52) U.S. Cl. ................................... 424/450; 428/402.2
(58) Field of Search .............................. 424/480, 1.21, 424/9.32, 9.51, 812, 417, 94.3; 436/829; 935/54; 428/402.2; 264/4.1, 4.3, 4.6

(56) References Cited

U.S. PATENT DOCUMENTS

| 4,089,801 A | * | 5/1978 | Schneider .................... 252/316 |
| 4,460,560 A | | 7/1984 | Tokes et al. ................. 424/1.1 |
| 4,501,728 A | | 2/1985 | Geho et al. .................... 424/38 |
| 4,534,899 A | | 8/1985 | Sears .......................... 260/403 |
| 4,544,545 A | | 10/1985 | Ryan et al. .................... 424/1.1 |
| 4,617,186 A | | 10/1986 | Schafer et al. ................. 424/78 |
| 4,650,909 A | | 3/1987 | Yoakum ....................... 568/621 |
| 4,737,323 A | | 4/1988 | Martin et al. ................. 264/4.3 |
| 4,752,425 A | | 6/1988 | Martin et al. ................. 264/4.6 |
| 4,837,028 A | | 6/1989 | Allen ........................... 424/450 |
| 4,861,521 A | | 8/1989 | Suzuki et al. ................. 260/403 |
| 4,920,016 A | | 4/1990 | Allen et al. .................. 424/450 |
| 4,943,624 A | | 7/1990 | Regen ......................... 528/301 |
| 4,944,948 A | | 7/1990 | Uster et al. .................. 424/450 |
| 4,963,367 A | | 10/1990 | Ecanow ....................... 424/485 |
| 5,008,109 A | | 4/1991 | Tin ............................. 424/422 |
| 5,013,556 A | | 5/1991 | Woodle et al. ............... 424/450 |
| 5,064,655 A | | 11/1991 | Uster et al. .................. 424/450 |
| 5,080,904 A | * | 1/1992 | Iga ............................. 424/450 |
| 5,094,819 A | | 3/1992 | Yager et al. ................. 422/82.7 |
| 5,153,000 A | | 10/1992 | Chikawa et al. ............. 424/450 |

(List continued on next page.)

FOREIGN PATENT DOCUMENTS

| CA | 2067133 | 4/1991 | |
| CA | 2067178 | 4/1991 | |
| CA | 2040237 | 10/1991 | ................. 167/163 |

(List continued on next page.)

OTHER PUBLICATIONS

Parr in BBA 1195, pp. 21–30, 1994.*
Abuchowski et al., "Treatment of L5178Y Tumor–Bearing BDF Mice with a Nonimmunogenic L–Glutaminase–L–Asparaginase," *Cancer Treatment Reports* 63(6): 1127–1132 (1979).

(List continued on next page.)

*Primary Examiner*—Gollamudi S. Kishore
(74) *Attorney, Agent, or Firm*—Townsend and Townsend and Crew LLP

(57) ABSTRACT

The present invention provides a fusogenic liposome comprising a lipid capable of adopting a non-lamellar phase, yet capable of assuming a bilayer structure in the presence of a bilayer stabilizing component; and a bilayer stabilizing component reversibly associated with the lipid to stabilize the lipid in a bilayer structure. Such fusogenic liposomes are extremely advantageous because the rate at which they become fusogenic can be not only predetermined, but varied as required over a time scale ranging from minutes to days. Control of liposome fusion can be achieved by modulating the chemical stability and/or exchangeability of the bilayer stabilizing component(s). The fusogenic liposomes of the present invention can be used to deliver drugs, peptide, proteins, RNA, DNA or other bioactive molecules to the target cells of interest.

21 Claims, 22 Drawing Sheets

(6 of 22 Drawing Sheet(s) Filed in Color)

U.S. PATENT DOCUMENTS

| | | | | |
|---|---|---|---|---|
| 5,190,761 A | | 3/1993 | Liburdy | 424/450 |
| 5,206,027 A | | 4/1993 | Kitaguchi | 424/450 |
| 5,213,804 A | * | 5/1993 | Martin | 424/450 |
| 5,225,212 A | | 7/1993 | Martin et al. | 424/450 |
| 5,264,221 A | * | 11/1993 | Tagawa | 426/450 |
| 5,356,633 A | | 10/1994 | Woodle et al. | 424/450 |
| 5,395,619 A | | 3/1995 | Zalipsky et al. | 424/450 |
| 5,527,528 A | | 6/1996 | Allen et al. | 424/178.1 |
| 5,552,155 A | * | 9/1996 | Bailey | 424/450 |
| 5,593,622 A | * | 1/1997 | Yoshioka | 264/432 |

FOREIGN PATENT DOCUMENTS

| | | | | |
|---|---|---|---|---|
| EP | 0118316 | 3/1983 | | C07F/9/10 |
| EP | 0072111 | 10/1985 | | |
| EP | 0220797 | 5/1987 | | |
| EP | 0370491 | 5/1990 | | |
| EP | 0422543 A1 | 4/1991 | | A61K/9/127 |
| EP | 0472543 | 4/1991 | | |
| EP | 0482860 | 4/1992 | | C07C/235/08 |
| EP | 0572049 | 1/1993 | | |
| EP | 0445131 | 4/1994 | | |
| EP | 0354855 | 12/1994 | | |
| EP | 0496813 | 12/1994 | | |
| EP | 0496835 | 5/1995 | | |
| GB | 2185397 | 7/1987 | | |
| WO | WO88/04924 | 7/1988 | | |
| WO | WO90/04384 | 5/1990 | | |
| WO | WO91/05545 | 5/1991 | | |
| WO | WO91/05546 | 5/1991 | | |
| WO | WO93/19738 | 10/1993 | | |
| WO | WO94/07466 | 4/1994 | | |
| WO | WO94/21281 | 9/1994 | | |
| WO | WO94/22429 | 10/1994 | | |
| WO | WO94/26251 | 11/1994 | | |
| WO | WO94/27580 | 12/1994 | | |
| WO | WO95/31183 | 11/1995 | | |
| WO | WO96/34598 | 11/1996 | | |

OTHER PUBLICATIONS

Abuchowski et al., "Immunosuppresive Properties and Circulating Life of Achromobacter Glutaminase–Asparaginase Covalently Attached to Polyethylene Glycol in Man," *Cancer Treatment Reports* 65(11–12): 1077–1081 (1981).

Berger et al., "Preparation of Polyethylene Glycol–Tissue Plasminogen Activator Adducts that Retain Functional Activity: Characteristics and Behavior in Three animal Species," *Blood*71(6): 1641–1647 (1988).

Allen, *Journal of Liposome Research Research*2(3):289–305 (1992).

Soehnlein et al., *Seifen, Ole, Fette, Wachse*115(3):85–86 (1989).

Connor et al., "pH–Sensitive Liposomes: Acid–Induced Liposome Fusion," *Proc. Nat. Acad. Sci. USA*81:1715–1718 (1984).

Silvius et al., "Interbilayer Transfer of Phospholipid–Anchored Macromolecules via Monomer Diffusion," *Biochemistry*32:3153–3161 (1993).

Hope and Cullis, "The Role of Nonbilayer Lipid Structures in the Fusion of Human Erythrocytes Induced by Lipid Fusogens," *Biochimica et Biophysica Acta*640:82–90 (1981).

Uster and Deamer, "Fusion Competence of Phosphatidylserine–Containing Liposomes Quantitatiely Measured by a Fluorescence Resonance Energy Transfer Assay," *Archives of Biochemistry and Biophysics*209:385–395 (1981).

Epand, "High Sensitivity Differential Scanning Calorimetry of the Bilayer to Hexagonal Phase Transitions of Diacylphosphatidylethanolamines," *Chemistry of Physics and Lipids*36:387–393 (1985).

Cullis and DeKrujiff, "Lipid Polymorphism and the Functional Roles of Lipids in Biological Membranes," *Biochimica et Biophysica Acta*559:399–420 (1979).

Madden and Cullis, "Stabilization of Bilayer Structure of Unsaturated Phosphatidylethanolamines by Detergents," *Biochimica et at Biophysica Acta*684:149–153 (1982).

Sleight and Pagano, "Transport of a Fluorescent Phosphatidylcholine Analog from the Plasma Membrane to the Golgi Apparatus," *Journal of Cell Biology*99:742–751 (1984).

Tsien and Pozzan, "Measurement of Cytosolic Free Ca2 with Quin2," *Methods in Enzymology*172:230–262 (1989).

Schroit et al., "The Recognition of Red Blood Cells by Macrophages: Role of Phosphatidylserine and Possible Implications of Membranes Phospholipid Asymmetry," *Biology of the Cell*51:227–238 (1984).

Minta et al., "Fluorescent Indicators for Cytosolic Calcium Based on Rhodamine and Fluorescein Chromophores," *Journal of Biological Chemistry*264(14): 8171–8178 (1989).

Duzgunes et al., "Proton–Induced Fusion of Oleic Acid––Phosphatidylethanolamine Liposomes," *Biochemistry*24:3091–3098 (1985).

Ellens et al., "H+–and Ca2+–Induced Fusion and Destabilization of Liposomes," *Biochemistry*24:3099–3106 (1985).

Hope et al., "Production of Large Unilamellar Vesicles by a Rapid Extrusion Procedure: Characterization of Size Distribution, Trapped Volume and Ability to Maintain a Membrane Potential," *Biochimica et Biophysica Acta*812:55–65 (1985).

Janoff et al., "Unusual Lipid Structures Selectively Reduce the Toxicity of Amphotericin B," *Proc. Natl. Acad. Sci. USA*85:6122–6126 (1988).

Madden et al. "Influence of Vesicle Size and Oxidase Content on Respiratory Control in Reconstituted Cytochrome Oxidase Vesicies," *Biochemistry*23:1413–1418 (1984).

Sato and Sunamoto, "Recent Aspects in the Use of Liposomes in Biotechnology and Medicine," *Prog. Lipid Res.*31(4):345–372 (1992).

Weder and Zumbuehl, "The Preparation of Variably Sized Homogeneous Liposomes for Laboratory, Clinical, and Industrial Use by Controlled Detergent Dialysis," *Liposome Technology*I:79–107.

Mimms et al., "Phospholipid Vesicle Formation and Transmembrane Protein Incorporation Using Ocryl Glucoside," *Biochemistry*20:833–840 (1981).

Handa et al., "Phospholipid Monolayers at the Triolein–Saline Interface: Production of Microemulsion Particles and Conversion of Monolayers to Bilayers," *Biochemistry*29: 2884–2890 (1999).

Klibanov and Huang, "Long–Circulating Liposomes: Development and Perspectives," *J. Liposome Res.*2(3):321–334 (1992).

Gao and Huang, "Cationic Liposomes and Polymers for Gene Transfer," *J. Liposome Res.*3(1):17–30 (1993).

Chu and Szoka, Jr. "pH–Sensitive Liposomes," *J. Liposome Res.*4(1):361–395 (1994).

Bally et al., "Polymorphism of Phosphatidylethanolamine––Phosophatidylserine Model Systems: Influence of Cholesterol and Mg2 on Ca2–Triggered Bilayer to Hexagonal (HII) Transitions," *Can. J. Biochem. Cell Biol.*61:346–352 (1983).

* cited by examiner

LIPOSOME HAVING AN EXCHANGEABLE COMPONENT

This application is a continuation of U.S. patent application Ser. No. 08/485,608, filed Jun. 7, 1995, now U.S. Pat. No. 5,885,613, which claims priority to U.S. application Ser. No. 08/316,407, filed Sep. 30, 1994.

BACKGROUND OF THE INVENTION

It is well recognized in the medical field that the most effective procedure for treating localized disease is to direct the pharmaceutical or drug agent (hereinafter "drugs") to the affected area, thereby avoiding undesirable toxic effects of systemic treatment. Techniques currently being used to deliver drugs to specific target sites within the body involve the utilization of time-release capsules or gel matrices from which drugs slowly "leak," or the use of implantable "syringes" that mechanically release drugs into muscles or into the blood stream. Another, and perhaps more effective delivery system, encompasses the use of liposomes containing the appropriate drug or chemical. The liposome with encapsulated drug is directed to the specific area of interest and, thereafter, the drug is released. The carrying out of this latter step is the most problematic and, in fact, the greatest barrier to the use of liposomes as drug carriers is making the liposomes release the drugs on demand at the target site of interest.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature, $T_c$. Current methods of drug delivery via liposomes require that the liposome carrier will ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Proc. Natl. Acad. Sci. USA 84:7851 (1987); Biochemistry 28:908 (1989)). When liposomes are endocytosed by a target cell, for example, they can be routed to acidic endosomes which will destabilize the liposome and result in drug release. Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

In addition to the foregoing methods, a liposome having a predetermined phase transition temperature, $T_c$, above body temperature can be used to achieve active drug delivery. In this method, the body temperature will maintain the liposome below the $T_c$ so that the liposome will not become leaky when placed in the body. This method of drug release is capable of "on demand" drug delivery since such liposomes experience a greatly increased membrane permeability at their $T_c$ which, in turn, enables drug or chemical release. To release drugs from such phase transition liposomes when in the body, heat must be applied until the $T_c$ is achieved. Unfortunately, the application of heat can, in itself, create problems within the body and, frequently, the adverse effects of the heat treatment outweigh the beneficial effects of using the liposome as a drug delivery vehicle. Moreover, such liposomes must be made of highly purified and expensive phase transition temperature phospholipid materials.

In view of the foregoing, there exists a need in the art for a method for targeted drug delivery that overcomes the disadvantages of the currently available methods. Specifically, a parenteral delivery system is required that would be stable in the circulation, following intravenous administration, allowing retention of encapsulated or associated drug or therapeutic agent(s). This delivery system would be capable of accumulating at a target organ, tissue or cell via either active targeting (e.g., by incorporating an antibody or hormone on the surface of the liposomal vehicle) or via passive targeting, as seen for long-circulating liposomes. Following accumulation at the target site, the liposomal carrier would become fusogenic, without the need for any external stimulus, and would subsequently release any encapsulated or associated drug or therapeutic agent in the vicinity of the target cell, or fuse with the target cell plasma membrane introducing the drug or therapeutic agent into the cell cytoplasm. In certain instances, fusion of the liposomal carrier with the plasma membrane would be preferred because this would provide more specific drug delivery and, hence, minimize any adverse effects on normal, healthy cells or tissues. In addition, in the case of therapeutic agents such as DNA, RNA, proteins, peptides, etc., which are generally not permeable to the cell membrane, such a fusogenic carrier would provide a mechanism whereby the therapeutic agent could be delivered to its required intracellular site of action. Further, by avoiding the endocytic pathway, the therapeutic agent would not be exposed to acidic conditions and/or degradative enzymes that could inactivate said therapeutic agent. Quite surprisingly, the present invention addresses this need by providing such a method.

SUMMARY OF THE INVENTION

The present invention provides a fusogenic liposome comprising a lipid capable of adopting a non-lamellar phase, yet capable of assuming a bilayer structure in the presence of a bilayer stabilizing component; and a bilayer stabilizing component reversibly associated with the lipid to stabilize the lipid in a bilayer structure. Such fusogenic liposomes are extremely advantageous because the rate at which they become fusogenic can be not only predetermined, but varied as required over a time scale ranging from minutes to days. Control of liposome fusion can be achieved by modulating the chemical stability and/or exchangeability of the bilayer stabilizing component(s).

Lipids which can be used to form the fusogenic liposomes of the present invention are those which adopt a non-lamellar phase under physiological conditions or under specific physiological conditions, e.g., in the presence of calcium ions, but which are capable of assuming a bilayer structure in the presence of a bilayer stabilizing component. Lipids which adopt a non-lamellar phase include, but are not limited to, phosphatidylenthanolamines, ceramides, glycolipids, or mixtures thereof. Such lipids can be stabilized in a bilayer structure by bilayer stabilizing components which are either bilayer forming themselves, or which are of a complementary dynamic molecular shape. More particularly, the bilayer stabilizing components of the present invention must be capable of stabilizing the lipid in a bilayer structure, yet they must be capable of exchanging out of the liposome, or of being chemically modified by endogenous systems so that, with time, they lose their ability to stabilize the lipid in a bilayer structure, thereby allowing the liposome to become fusogenic. Only when liposomal stability is lost or decreased can fusion of the liposome with the plasma membrane of the target cell occur.

By controlling the composition and concentration of the bilayer stabilizing component, one can control the chemical stability of the bilayer stabilizing component and/or the rate at which the bilayer stabilizing component exchanges out of the liposome and, in turn, the rate at which the liposome becomes fusogenic. In addition, other variables including, for example, Ph, temperature, ionic strength, etc. can be used to vary and/or control the rate at which the liposome becomes fusogenic.

The fusogenic liposomes of the present invention are ideally suited to a number of therapeutic, research and commercial applications. In therapeutic applications, for example, the initial stability of the fusogenic liposome would allow time for the liposome to achieve access to target organs or cells before attaining its fusogenic state, thereby reducing non-specific fusion immediately following administration.

In addition, the fusogenic liposomes of the present invention can be used to deliver drugs, peptide, proteins, RNA, DNA or other bioactive molecules to the target cells of interest. In this embodiment, the compound or molecule to be delivered to the target cell can be encapsulated in the aqueous interior of the fusogenic liposome and subsequently introduced into the cytoplasma (initially) upon fusion of the liposome with the cell plasma membrane. Alternatively, molecules or compounds can be embedded within the liposome bilayer and, in this case, they would be incorporated into the target cell plasma membrane upon fusion.

As such, in another embodiment, the present invention provides a method for delivering a therapeutic compound to a target cell at a predetermined rate, the method comprising: administering to a host containing the target cell a fusogenic liposome which comprises a bilayer stabilizing component, a lipid capable of adopting a non-lamellar phase, yet capable of assuming a bilayer structure in the presence of the bilayer stabilizing component, and a therapeutic compound or a pharmaceutically acceptable salt thereof. Administration may be by a variety of routes, but the therapeutic compounds are preferably given intravenously or parenterally. The fusogenic liposomes administered to the host may be unilamellar, having a mean diameter of 0.05 to 0.45 microns, more preferably from 0.05 to 0.2 microns.

In a final embodiment, the present provides a method of stabilizing in a bilayer structure a lipid which is capable of adopting a non-lamellar phase by combining the lipid(s) with a bilayer stabilizing component. Once stabilized, the lipid mixture can be used to form the fusogenic liposomes of the present invention. The bilayer stabilizing component is selected, however, to be exchangeable such that upon loss of this component from the liposome, the liposome is destabilized and becomes fusogenic.

Other features, objects and advantages of the invention and its preferred embodiments will become apparent from the detailed description which follows.

BRIEF DESCRIPTION OF THE DRAWINGS

There is at least one color drawing in this application.

DETAILED DESCRIPTION OF THE INVENTION AND PREFERRED EMBODIMENTS

Figure 1:
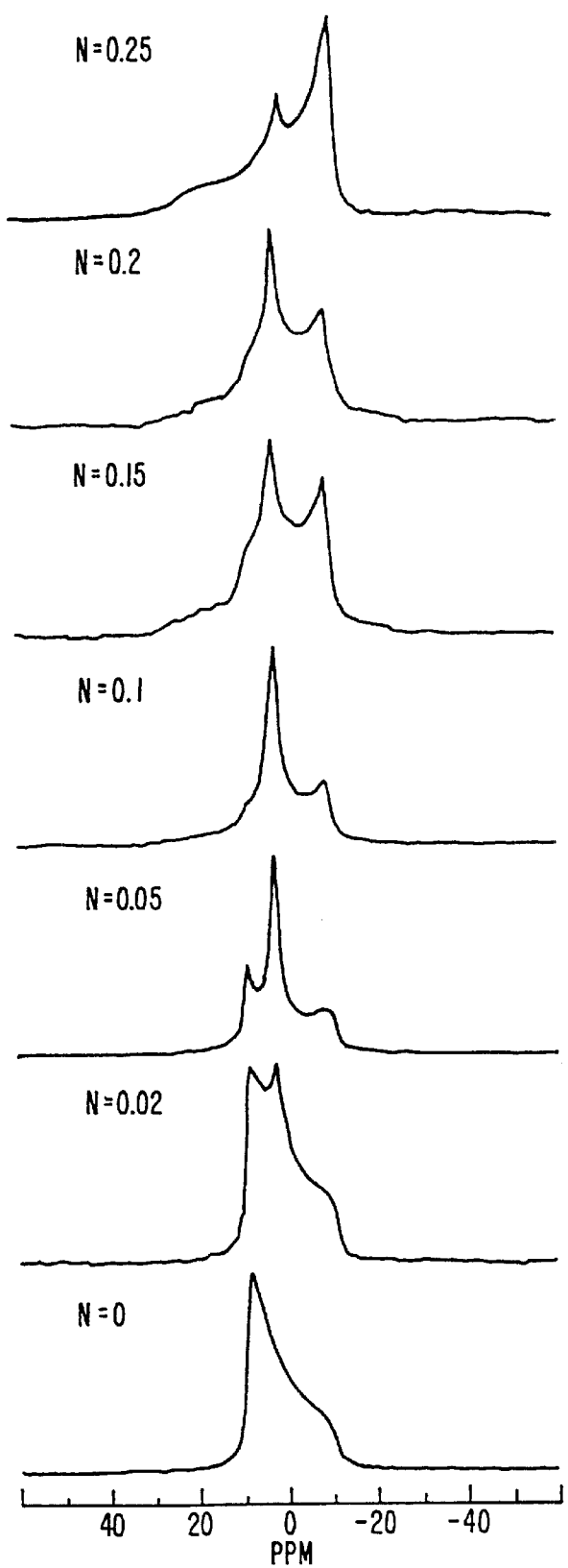
FIG. 1 illustrates the concentration dependence of bilayer stabilization by a bilayer stabilizing component (BSC). Multilamellar vesicles were prepared, as described in the examples, from mixtures of DOPE:cholesterol:DOPE-PEG$_{2000}$, 1:1:N, where N is the proportion of DOPE-PEG$_{2000}$ as indicated in the FIG. 1. $^{31}$P-NMR spectra were determined at 20° C. after the sample had been allowed to equilibrate for 30 minutes.

In one embodiment of the present invention, a fusogenic liposome is provided, the fusogenic liposome comprising: a lipid capable of adopting a non-lamellar phase, yet capable of assuming a bilayer structure in the presence of a bilayer stabilizing component; and a bilayer stabilizing component reversibly associated with the lipid to stabilize the lipid in a bilayer structure. Such fusogenic liposomes are advantageous because the rate at which they become fusogenic can be not only predetermined, but varied as required over a time scale of a few minutes to several tens of hours. It has been found, for example, that by controlling the composition and concentration of the bilayer stabilizing component, one can control the rate at which the bilayer stabilizing component exchanges out of the liposome and, in turn, the rate at which the liposome becomes fusogenic.

The polymorphic behavior of lipids in organized assemblies can be explained qualitatively in terms of the dynamic molecular shape concept (see, Cullis et al., in "Membrane Fusion" (Wilschut, J. and D. Hoekstra (eds.), Marcel Dekker, Inc., New York, (1991)). When the effective cross-sectional areas of the polar head group and the hydrophobic region buried within the membrane are similar then the lipids have a cylindrical shape and tend to adopt a bilayer conformation. Cone-shaped lipids which have polar head groups that are small relative to the hydrophobic component, such as unsaturated phosphatidylethanolamines, prefer non-bilayer phases such as inverted micelles or inverse hexagonal phase ($H_{II}$). Lipids with head groups that are large relative to their hydrophobic domain, such as lysophospholipids, have an inverted cone shape and tend to form micelles in aqueous solution. The phase preference of a mixed lipid system depends, therefore, on the contributions of all the components to the net dynamic molecular shape. As such, a combination of cone-shaped and inverted cone-shaped lipids can adopt a bilayer conformation under conditions where either lipid in isolation cannot (see, Madden and Cullis, *Biochim. Biophys. Acta*, 684:149–153 (1982)).

A more formalized model is based on the intrinsic curvature hypothesis (see, e.g., Kirk, et al., *Biochemistry*, 23:1093–1102 (1984)). This model explains phospholipid polymorphism in terms of two opposing forces. The natural tendency of a lipid monolayer to curl and adopt its intrinsic or equilibrium radius of curvature ($R_o$) which results in an elastically relaxed monolayer is opposed by the hydrocarbon packing constraints that result. Factors that decrease the intrinsic radius of curvature, such as increased volume occupied by the hydrocarbon chains when double bonds are introduced, tend to promote $H_{II}$ phase formation. Conversely, an increase in the size of the headgroup increases $R_o$ and promotes bilayer formation or stabilization. Introduction of apolar lipids that can fill the voids between inverted lipid cylinders also promotes $H_{II}$ phase formation (see, Gruner, et al., *Proc. Natl. Acad. Sci. USA*, 82:3665–3669 (1989); Sjoland, et al., *Biochemistry*, 28:1323–1329 (1989)).

Lipids which can be used to form the fusogenic liposomes of the present invention are those which adopt a non-lamellar phase under physiological conditions or under specific physiological conditions, e.g., in the presence of calcium ions, but which are capable of assuming a bilayer structure in the presence of a bilayer stabilizing component. Such lipids include, but are not limited to, phosphatidylenthanolamines, ceramides, glycolipids, or mixtures thereof. Other lipids known to those of skill in the art to adopt a non-lamellar phase under physiological conditions can also be used. Moreover, it will be readily apparent to those of skill in the art that other lipids can be induced to adopt a non-lamellar phase by various non-physiological changes including, for example, changes in pH or ion concentration (e.g., in the presence of calcium ions) and, thus, they can also be used to form the fusogenic liposomes of the present invention. In a presently preferred embodiment, the fusogenic liposome is prepared from a phosphatidylethanolamine. The phosphatidylethanolamine can be saturated or unsaturated. In a presently preferred embodiment, the phosphatidylyethanolamine is unsaturated. In an equally preferred embodiment, the fusogenic liposome is prepared from a mixture of a phosphatidylethanolamine (saturated or unsaturated) and a phosphatidylserine. In another equally preferred embodiment, the fusogenic liposome is prepared from a mixture of a phosphatidylethanolamine (saturated or unsaturated) and a cationic lipid.

Examples of suitable cationic lipids include, but are not limited to, the following: DC-Chol, 3β-(N-(N',N'-dimethylaminoethane)carbamoyl)cholesterol (see, Gao, et al., *Biochem. Biophys. Res. Comm* 179:280–285 (1991); DDAB, N,N-distearyl-N,N-dimethylammonium bromide; DMRIE, N-(1,2dimyristyloxypro-3-yl)-N,N-dimethyl-N-hydroxyethyl ammonium bromide; DODAC, N,N-dioleyl-N,N-dimethylammonium chloride (see, commonly owned U.S. patent application Ser. No. 08/316,399, filed Sep. 30, 1994, which is incorporated herein by reference); DOGS, diheptadecylamidoglycyl spermidine; DOSPA, N-(1-(2,3-dioleyloxy)propyl)-N-(2-(sperminecarboxamido)ethyl)-N, N-dimethylammonium trifluoroacetate; DOTAP, N-(1-(2,3-dioleoyloxy)propyl)-N,N,N-trimethylammonium chloride; and DOTMA, N-(1-(2,3-dioleyloxy)propyl)-N,N,N-trimethylammonium chloride. In a presently preferred embodiment, N,N-dioleoyl-N,N-dimethylammonium chloride is used in combination with a phosphatidylethanolamine.

In accordance with the present invention, lipids adopting a non-lamellar phase under physiological conditions can be stabilized in a bilayer structure by bilayer stabilizing components which are either bilayer forming themselves, or which are of a complementary dynamic shape. The non-bilayer forming lipid is stabilized in the bilayer structure only when it is associated with, i.e., in the presence of, the bilayer stabilizing component. In selecting an appropriate bilayer stabilizing component, it is imperative that the bilayer stabilizing component be capable of transferring out of the liposome, or of being chemically modified by endogenous systems such that, with time, it loses its ability to stabilize the lipid in a bilayer structure. Only when liposomal stability is lost or decreased can fusion of the liposome with the plasma membrane of the target cell occur. The bilayer stabilizing component is, therefore, "reversibly associated" with the lipid and only when it is associated with the lipid is the lipid constrained to adopt the bilayer structure under conditions where it would otherwise adopt a non-lamellar phase. As such, the bilayer stabilizing components of the present invention must be capable of stabilizing the lipid in a bilayer structure, yet they must be capable of exchanging out of the liposome, or of being chemically modified by endogenous systems so that, with time, they lose their ability to stabilize the lipid in a bilayer structure, thereby allowing the liposome to become fusogenic.

Examples of suitable bilayer stabilizing components include, but are not limited to, lipid, lipid-derivatives, detergents, proteins and peptides. In a presently preferred embodiment, the bilayer stabilizing component is polyethyleneglycol conjugated to, i.e., coupled to, a phosphatidylethanolamine. In an equally preferred embodiment, the bilayer stabilizing component is polyethyleneglycol conjugated to a ceramide. Polyethyleneglycol can be conjugated to a phosphatidylethanolamine or, alternatively, to a ceramide using standard coupling reactions known to and used by those of skill in the art. In addition, preformed polyethyleneglycol-phosphatidylethanolamine conjugates are commercially available from Avanti Polar Lipids (Alabaster, Ala.).

Polyethyleneglycols of varying molecular weights can be used to form the bilayer stabilizing components of the present invention. Polyethyleneglycols of varying molecular weights are commercially available from a number of different sources or, alternatively, they can be synthesized using standard polymerization techniques well-known to those of skill in the art. In a presently preferred embodiment, the polyethylene glycol has a molecular weight ranging from about 200 to about 10,000, more preferably from about 1,000 to about 8,000, and even more preferably from about 2,000 to about 6,000. Generally, it has been found that increasing the molecular weight of the polyethyleneglycol reduces the concentration of the bilayer stabilizing component required to achieve stabilization.

Phosphatidylethanolamines having a variety of acyl chain groups of varying chain lengths and degrees of saturation can be conjugated to polyethyleneglycol to form the bilayer stabilizing component. Such phosphatidylethanolamines are commercially available, or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidyl-ethanolamine (DSPE).

As with the phosphatidylethanolamines, ceramides having a variety of acyl chain groups of varying chain lengths and degrees of saturation can be coupled to polyethyleneglycol to form the bilayer stabilizing component. It will be apparent to those of skill in the art that in contrast to the phosphatidylethanoiamines, ceramides have only one acyl group which can be readily varied in terms of its chain length and degree of saturation. Ceramides suitable for use in accordance with the present invention are commercially available. In addition, ceramides can be isolated, for example, from egg or brain using well-known isolation techniques or, alternatively, they can be synthesized using the methods and techniques disclosed in U.S. patent application Ser. No. 08/316,429, filed Sep. 30, 1994, and U.S. Patent Application filed on an even date herewith and bearing Attorney Docket No. 16303-001010, the teachings of which are incorporated herein by reference. Using the synthetic routes set forth in the foregoing application, ceramides having saturated or unsaturated fatty acids with carbon chain lengths in the range of $C_2$ to $C_{31}$ can be prepared.

In addition to the foregoing, detergents, proteins and peptides can be used as bilayer stabilizing components. Detergents which can be used as bilayer stabilizing components include, but are not limited to, Triton X-100, deoxycholate, octylglucoside and lyso-phosphatidylcholine. Proteins which can be used as bilayer stabilizing components include, but are not limited to, glycophorin and cytochrome oxidase. Cleavage of the protein, by endogenous proteases, resulting in the loss of the bullcy domain external to the bilayer would be expected to reduce the bilayer stabilizing ability of the protein. In addition, peptides which can be used as bilayer stabilizing components include, for example, the pentadecapeptide, alanine-(aminobutyric acid-alanine)$_{14}$. This peptide can be coupled, for example, to polyethyleneglycol which would promote its transfer out of the bilayer. Alternatively, peptides such as cardiotoxin and melittin, both of which are known to induce non-lamehlar phases in bilayers, can be coupled to PEG and might thereby be converted to bilayer stabilizers in much the same way that PE is converted from a non-lamellar phase preferring lipid to a bilayer stabilizer when it is coupled to PEG. If the bond between the peptide and the PEG is labile, then cleavage of the bond would result in the loss of the bilayer stabilizing ability and in the restoration of a non-lamellar phase, thereby causing the liposome to become fusogenic.

Typically, the bilayer stabilizing component is present at a concentration ranging from about 0.05 mole percent to about 50 mole percent. In a presently preferred embodiment, the bilayer stabilizing component is present at a concentration ranging from 0.05 mole percent to about 25 mole percent. In an even more preferred embodiment, the bilayer stabilizing component is present at a concentration ranging from 0.05 mole percent to about 15 mole percent. One of ordinary skill in the art will appreciate that the concentration of the bilayer stabilizing component can be varied depending on the bilayer stabilizing component employed and the rate at which the liposome is to become fusogenic.

By controlling the composition and concentration of the bilayer stabilizing component, one can control the rate at which the bilayer stabilizing component exchanges out of the liposome and, in turn, the rate at which the liposome becomes fusogenic. For instance, when a polyethyleneglycol-phosphatidylethanolamine conjugate or a polyethyleneglycol-ceramide conjugate is used as the bilayer stabilizing component, the rate at which the liposome becomes fusogenic can be varied, for example, by varying the concentration of the bilayer stabilizing component, by varying the molecular weight of the polyethyleneglycol, or by varying the chain length and degree of saturation of the acyl chain groups on the phosphatidylethanolamine or the ceramide. In addition, other variables including, for example, pH, temperature, ionic strength, etc. can be used to vary and/or control the rate at which the liposome becomes fusogenic. Other methods which can be used to control the rate at which the liposome becomes fusogenic will become apparent to those of skill in the art upon reading this disclosure.

In a presently preferred embodiment, the fusogenic liposomes contain cholesterol. It has been determined that when cholesterol-free liposomes are used in vivo, they have a tendency to absorb cholesterol from plasma lipoproteins and cell membranes. Since this absorption of cholesterol could, in theory, change the fusogenic behavior of the liposomes, cholesterol can be included in the fusogenic liposomes of the present invention so that little or no net transfer of cholesterol occurs in vivo. Cholesterol, if included, is generally present at a concentration ranging from 0.02 mole percent to about 50 mole percent and, more preferably, at a concentration ranging from about 35 mole percent to about 45 mole percent.

A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer and Bangham, *Biochim. Biophys. Acta*, 443:629–634 (1976); Fraley, et al., *Proc. Natl. Acad. Sci. USA* 76:3348–3352 (1979); Hope, et al., *Biochim. Biophys. Acta* 812:55–65 (1985); Mayer, et al., *Biochim. Biophys. Acta* 858:161–168 (1986); Williams, et al., *Proc. Natl. Acad. Sci. USA* 85:242–246 (1988); the text Liposomes, (Marc J. Ostro (ed.), Marcel Dekker, Inc., New York, 1983, Chapter 1); and Hope, et al., *Chem. Phys. Lip.* 40:89 (1986), all of which are incorporated herein by reference. Suitable methods include, for example, sonication, extrusion, high pressure/homogenization, microfluidization, detergent dialysis, calcium-induced fusion of small liposome vesicles and ether-fusion methods, all of which are well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Unilamellar vesicles are generally prepared by sonication or extrusion. Sonication is generally preformed with a tip sonifier, such as a Branson tip sonifier, in an ice bath. Typically, the suspension is subjected to several sonication cycles. Extrusion can be carried out by biomembrane extruders, such as the Lipex Biomembrane Extruder. Defined pore size in the extrusion filters can generate unilamellar liposomal vesicles of specific sizes. The liposomes can also be formed by extrusion through an asymmetric ceramic filter, such as a Ceraflow Microfilter, commercially available from the Norton Company, Worcester Mass.

Following liposome preparation, the liposomes may be sized to achieve a desired size range and relatively narrow distribution of liposome sizes. A size range of about 0.05 microns to about 0.20 microns allows the liposome suspension to be sterilized by filtration through a conventional filter, typically a 0.22 micron filter. The filter sterilization method can be carried out on a high through-put basis if the liposomes have been sized down to about 0.05 microns to about 0.20 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both of these methods, the particle size distribution can be monitored by conventional laser-beam particle size discrimination. In addition, the size of the liposomal vesicle can be determined by quasi-electric light scattering (QELS) as described in Bloomfield, *Ann. Rev. Biophys. Bioeng.* 10:421–450 (1981), incorporated herein by reference. Average liposome diameter can be reduced by sonication of formed liposomes. Intermittent sonication cycles can be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present inventions, liposomes having a size of from about 0.05 microns to about 0.45 microns are preferred.

For the delivery of therapeutic agents, the fusogenic liposomes of the present invention can be loaded with a therapeutic agent and administered to the subject requiring treatment. The therapeutic agents which can be administered using the fusogenic liposomes of the present invention can be any of a variety of drugs, peptides, proteins, DNA, RNA or other bioactive molecules. Moreover, cationic lipids may be used in the delivery of therapeutic genes or oligonucleotides intended to induce or to block production of some protein within the cell. Nucleic acid is negatively charged and must be combined with a positively charged entity to form a complex suitable for formulation and cellular delivery.

Cationic lipids have been used in the transfection of cells in vitro and in vivo (Wang, C-Y, Huang L., "pH sensitive immunoliposomes mediate target cell-specific delivery and controlled expression of a foreign gene in mouse," *Proc. Natl. Acad. Sci. USA*, 1987; 84:7851–7855 and Hyde, S. C., Gill, D. R., Higgins, C. F., et al., "Correction of the ion transport defect in cystic fibrosis transgenic mice by gene therapy," *Nature*, 1993; 362:250–255). The efficiency of this transfection has often been less than desired, for various reasons. One is the tendency for cationic lipids complexed to nucleic acid to form unsatisfactory carriers. These carriers are improved by the inclusion of PEG lipids.

Cationic lipids useful in producing lipid based carriers for gene and oligonucleotide delivery include, but are not limited to, 3β-(N-(N',N'-dimethylaminoethane)carbamoyl) cholesterol (DC-Chol); N,N-distearyl-N,N-dimethylammonium bromide (DDAB); N-(1,2-dimyristyloxyprop-3-yl)-N,N-dimethyl-N-hydroxyethyl ammonium bromide (DMRIE); diheptadecylamidoglycyl spermidine (DOGS); N-(1-(2,3-dioleyloxy)propyl)-N-(2-(sperminecarboxamido)ethyl)-N,N-dimethylammonium trifluoroacetate (DOSPA); N-(1-(2,3-dioleoyloxy)propyl)-N,N,N-trimethylammonium chloride (DOTAP); N-(1-(2,3-dioleyloxy)propyl)-N,N,N-trimethylammonium chloride (DOTMA); N,N-dioleyl-N,N-dimethylammonium chloride (DODAC); LIPOFECTIN, a commercially available cationic lipid comprising DOTMA and DOPE (GIBCO/BRL, Grand Island, N.Y.) (U.S. Pat. Nos. 4,897,355; 4,946,787; and 5,208,036 issued to Epstein, et al.); LIPOFECTACE or DDAB (dimethyldioctadecyl ammonium bromide) (U.S. Pat. No. 5,279,883 issued to Rose); LIPOFECTAMINE, a commercially available cationic lipid composed of DOSPA and DOPE (GIBCO/BRL, Grand Island, N.Y.); TRANSFECTAM, a commercially available cationic lipid comprising DOGS (Promega Corp., Madison, Wis.).

Any variety of drugs which are selected to be an appropriate treatment for the disease to be treated in the tissue can be administered using the fusogenic liposomes of the present invention. Often the drug will be an antineoplastic agent, such as vincristine, doxorubicin, cisplatin, bleomycin, cyclophosphamide, methotrexate, streptozotocin, and the like. It may also be desirable to deliver anti-infective agents to specific tissues by the present methods. The compositions of the present invention can also be used for the selective delivery of other drugs including, but not limited to local anesthetics, e.g., dibucaine and chlorpromazine; beta-adrenergic blockers, e.g., propranolol, timolol and labetolol; antihypertensive agents, e.g., clonidine and hydralazine; anti-depressants, e.g., imipramine, amitriptyline and doxepim; anti-convulsants, e.g., phenytoin; antihistamines, e.g., diphenhydramine, chlorphenirimine and promethazine; antibacterial agents, e.g., gentamycin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents. Other particular drugs which can be selectively administered by the compositions of the present invention will be well known to those of skill in the art. Additionally, two or more therapeutic agents may be administered simultaneously if desired, where such agents produce complementary or synergistic effects.

Methods of loading conventional drugs into liposomes include an encapsulation technique and the transmembrane potential loading method. In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. No. 4,885,172, U.S. Pat. No. 5,059,421, and U.S. Pat. No. 5,171,578, the contents of which are incorporated herein by reference. Briefly, the transmembrane potential loading method can be used with essentially any conventional drug which exhibits weak acid or weak base characteristics. Preferably, the drug will be relatively lipophilic so that it will partition into the liposome membrane. A pH gradient is created across the bilayers of the liposomes or protein-liposome complexes, and the drug is loaded into the liposome in response to the pH gradient. The pH gradient is generated by creating a proton gradient across the membrane either by making the interior more acidic or basic than the exterior (Harrigan, et al., *Biochem. Biophys. Acta.* 1149:329–339 (1993), the teachings of which are incorporated herein by reference), or by establishing an ion gradient employing ionizable agents, such as ammonium salts, which leads to the generation of a pH gradient (See, U.S. Pat. No. 5,316,771 (Barenholz), the teachings of which are incorporated herein by reference).

In certain embodiments of the present invention, it is desirable to target the liposomes of the invention using targeting moieties that are specific to a particular cell type, tissue, and the like. Targeting of liposomes using a variety of targeting moieties (e.g., ligands, receptors and monoclonal antibodies) has been previously described (see, e.g., U.S. Pat. Nos. 4,957,773 and 4,603,044, both of which are incorporated herein by reference).

Examples of targeting moieties include monoclonal antibodies specific to antigens associated with neoplasms, such as prostate cancer specific antigen. Tumors can also be diagnosed by detecting gene products resulting from the activation or overexpression of oncogenes, such as ras or c-erB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see, Renneisen, et al., *J. Biol. Chem.*, 265:16337–16342 (1990) and Leonetti, et al., *Proc. Natl. Acad. Sci.* (*USA*) 87:2448–2451 (1990), both of which are incorporated herein by reference).

Targeting mechanisms generally require that the targeting agents be positioned on the surface of the liposome in such a manner that the target moieties are available for interaction with the target, for example, a cell surface receptor. The liposome is typically fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the target agent which is extended, three dimensionally, off of the vesicle surface.

Following a separation step as may be necessary to remove free drug from the medium containing the liposome, the liposome suspension is brought to a desired concentration in a pharmaceutically acceptable carrier for administration to the patient or host cells. Many pharmaceutically acceptable carriers may be employed in the compositions and methods of the present invention. Suitable formulations for use in the present invention are found in *Remington's Pharmaceutical Sciences*, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135–150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilied, the lyophilized preparation being combined with a sterile aqueous solution prior to administration.

The concentration of liposomes in the carrier may vary. Generally, the concentration will be about 20–200 mg/ml, usually about 50–150 mg/ml, and most usually about 75–125 mg/ml, e.g., about 100 mg/ml. Persons of skill may vary these concentrations to optimize treatment with different liposome components or for particular patients. For example, the concentration may be increased to lower the fluid load associated with treatment.

The present invention also provides methods for introducing therapeutic compounds into cells of a host. The methods generally comprise administering to the host a fusogenic liposome containing the therapeutic compound, wherein the fusogenic liposome comprises a bilayer stabilizing component and a lipid which adopts a non-lamellar phase under physiological conditions, yet which is capable of assuming a bilayer structure in the presence of said bilayer stabilizing component. The host may be a variety of animals, including humans, non-human primates, avian species, equine species, bovine species, swine, lagomorpha, rodents, and the like.

The cells of the host are usually exposed to the liposomal preparations of the invention by in vivo administration of the formulations, but ex vivo exposure of the cells to the liposomes is also feasible. In vivo exposure is obtained by administration of the liposomes to host. The liposomes may be administered in many ways. These include parenteral routes of administration, such as intravenous, intramuscular, subcutaneous, and intraarterial. Generally, the liposomes will be administered intravenously or in some cases via inhalation. Often, the liposomes will be administered into a large central vein, such as the superior vena cava or inferior vena cava, to allow highly concentrated solutions to be administered into large volume and flow vessels. The liposomes may be administered intraarterially following vascular procedures to deliver a high concentration directly to an affected vessel. In some instances, the liposomes may be administered orally or transdermally, although the advantages of the present invention are best realized by parenteral administration. The liposomes may also be incorporated into implantable devices for long duration release following placement.

As described above, the liposomes will generally be administered intravenously or via inhalation in the methods of the present invention. Often multiple treatments will be given to the patient. The dosage schedule of the treatments will be determined by the disease and the patient's condition. Standard treatments with therapeutic compounds that are well known in the art may serve as a guide to treatment with liposomes containing the therapeutic compounds. The duration and schedule of treatments may be varied by methods well known to those of skill, but the increased circulation time and decreased in liposome leakage will generally allow the dosages to be adjusted downward from those previously employed. The dose of liposomes of the present invention may vary depending on the clinical condition and size of the animal or patient receiving treatment. The standard dose of the therapeutic compound when not encapsulated may serve as a guide to the dose of the liposome-encapsulated compound. The dose will typically be constant over the course of treatment, although in some cases the dose may vary. Standard physiological parameters may be assessed during treatment that may be used to alter the dose of the liposomes of the invention.

Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and, thus, having shorter half-lives in the bloodstream. Liposomes with prolonged circulation half-lives are typically desirable for therapeutic and diagnostic uses. To maximize circulation half-lives, the bilayer stabilizing component should be a hydrophilic polymer, e.g., PEG, conjugated to lipid anchors, e.g., PEs, having long, saturated hydrocarbon chains (C18>C16>C14) as these conjugates provide a longer lasting steric barrier. As such, by varying the charge in addition to the foregoing factors, one of skill in the art can regulate the rate at which the liposomes of the present invention become fusogenic.

Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The invention will be described in greater detail by way of specific examples. The following examples are offered for illustrative purposes, and are not intended to limit the invention in any manner.

EXAMPLES

I. Materials and General Methods

A. Materials

All phospholipids including fluorescent probes and PEG-PE conjugates were purchased from Avanti Polar Lipids, Birmingham, Ala., USA. 1-O-methyl-(poly(ethoxy)-O-succinyl-O-(egg)ceramide which was a gift from Dr L. Choi of Inex Pharmaceuticals Corp., Vancouver, BC, Canada. Di-[1-$^{14}$C]-palmitoylphosphatidyl-choline was purchased from Du Pont, Mississauga, Ont., Canada. [$^3$H]-DSPE-PEG$_{2000}$ was synthesized as described previously (Parr, et al., *Biochim. Biophys. Acta*, 1195: 21–30 (1994)). Other reagents were purchased from Sigma Chemical Co., St Louis, Mo., USA.

B. Preparation of Multilamellar Vesicles and Large Unilamellar Vesicles

Lipid components were mixed in 1–2 ml of benzene:methanol (95:5, v/v) and then lyophilized for a minimum of 5 hours at a pressure of <60 millitorr using a Virtis lyophilizer equipped with a liquid N$_2$ trap. Multilamellar vesicles (MLVs) were prepared by hydrating the dry lipid mixtures in 150 mM NaCl, buffered with 10 mM Hepes-NaOH, pH 7.4 (Hepes-buffered saline, HBS). Mixtures were vortexed to assist hydration. To produce large unilamellar vesicles (LUVs), MLVs were first frozen in liquid nitrogen and then thawed at 30° C. five times. LUVs were produced by extrusion of the frozen and thawed MLVs ten times through 2 stacked polycarbonate filters of 100 nm pore size at 30° C. and pressures of 200–500 psi (Hope, et al., *Biochim. Biophys. Acta*, 812:55–65 (1985)).

C. $^{31}$P-NMR Spectroscopy $^{31}$P-NMR spectra were obtained using a temperature controlled Bruker MSL200 spectrometer operating at 81 MHz. Free induction decays were accumulated for 2000 transients using a 4 µs, 90° pulse, 1 sec. interpulse delay, 20 KHz sweep width and Waltz decoupling. A 50 Hz line broadening was applied to the data prior to Fourier transformation. Samples were allowed to equilibrate at the indicated temperature for 30 minutes prior to data accumulation. Lipid concentrations of 30–70 mM were used.

D. Freeze-fracture Electron Microscopy

MLVs were prepared by hydrating a mixture of DOPE:cholesterol:DOPE-PEG$_{2000}$ (1:1:0:1) with HBS. A portion of the mixture was extruded as described above to produce LUVs. Glycerol was added to both MLVs and LUVs to a final concentration of 25% and samples were rapidly frozen in liquid freon. The samples were fractured at –110° C. and <10$^{-6}$ torr in a Balzers BAF400 unit. Replicas were prepared by shadowing at 45° with a 2 nm layer of platinum and coating at 90° with a 20 nm layer of carbon. The replicas were cleaned by soaking in hypochlorite solution for up to 48 hrs and were visualized in a Jeol JEM-1200 EX electron microscope.

E. Gel Filtration of LUVs and Micelles

LUVs composed of DOPE:cholesterol:DSPE-PEG$_{2000}$ (1:1:0:1) with trace amounts of $^{14}$C-DPPC and $^{3}$H-DSPE-PEG$_{2000}$ were chromatographed at a flow rate of approximately 0.5 ml/min on a column of Sepharose CL-4B was pretreated with 10 mg of eggPC, which had been suspended in HBS by bath sonication, to eliminate non-specific adsorption of lipid to the column. Micelles were prepared by hydrating DSPE-PEG$_{2000}$ containing a trace amount of $^{3}$H-DSPE-PEG$_{2000}$ with HBS and chromatographed as described for LUVs.

F. Lipid Mixing Assays

Lipid mixtures were prepared as described for NMR measurements. The resultant multilamellar vesicles (MLV) were frozen in liquid nitrogen and then thawed at 30° C. five times. Large unilamellar vesicles (LUV) were produced by extrusion of the frozen and thawed MLV ten times through 2 stacked polycarbonate filters of 100 mn pore size at 30° C. and pressures of 200–500 psi (Hope, et al., *Biochim. Biophys. Acta* 812:55–65 (1985)).

Lipid mixing was measured by a modification of the fluorescence resonance energy transfer (FRET) assay of Struck, et al. (*Biochemistry* 20:4093–4099 (1981)). LUVs were prepared containing the fluorescent lipids, N-(7-nitro-2-1,3-benzoxadiazol-4-yl)-dioleoylphosphatidylethanolamine (NBD-PE) and N-(lissamine rhodamine B sulfonyl)-dipalmitoylphosphatidylethanolamine (Rh-PE) at 0.5 mol %. LUVs (50–60 µM) and a three-fold excess of unlabelled target vesicles were mixed in the fluorimeter at 37° C. for short term assays ($\leq$1 hour), or in sealed cuvettes in a dark water bath at 37° C. for longer assays. For measurements of fusion after PEG-lipid transfer, an excess of liposomes prepared from 1-palmitoyl-2-oleoyl-phosphatidylcholine (POPC) was added as a sink for the PEG-lipid. Fluorescence emission intensity was measured at 517 nm with excitation at 465 nm both before and after the addition of Triton X-100 (final concentration of 0. 5% or 1% when POPC sink was used). Data is presented as either uncorrected fluorescence intensity for short term assays (<1 hour) or as percentage fusion. Light scattering controls were performed by replacing LUVs labelled with 0.5 mol % probes with unlabelled vesicles. Maximum fusion was determined using mock fused vesicles containing 0.125 mol % of each fluorescent probe. The percentage fusion was calculated as:

$$\% \text{ Fusion} = \frac{\frac{(F_{(t)} - L_{(t)})}{(F_T - L_T)} - \frac{(F_O - L_O)}{(F_T - L_T)}}{\frac{(M_{(t)} - L_{(t)})}{(M_T - L_T)} - \frac{(F_O - L_O)}{(F_T - L_T)}} \times 100$$

where $F_{(t)}$=fluorescence intensity at time t; $F_o$=fluorescence intensity at zero time; $F_T$=fluorescence intensity in the presence of Triton X-100. M and L represent the same measurements for the mock fused control and the light scattering control respectively. Changes in fluorescence of the mock fused control indicated that exchange of the fluorescent probes over 24 hours accounted for 10% of the fluorescence change observed, but was negligible over the first hour.

G. Fusion of Liposomes with Red Blood Cells

LUVs composed of DOPE:cholesterol:DODAC (40:45:15) or DOPE:cholesterol:DODAC:PEG-ceramide (35:45:15:) were prepared by standard extrusion techniques. LUVs also contained 1 mol % rhodamine-PE. LUVs (200 /M) were incubated at 37° C. with 50 µl packed RBCs in a final volume of 1 ml. For assays of fusion after PEG-lipid exchange, a sink of 2 mM POPC:cholesterol (55:45) was included. In some assays, the fusogenic liposomes were pre-incubated with the sink before being mixed with the RBCs (See, figure legends for FIGS. 22–24). Aliquots of the mixtures were transferred to glass microscope slides, covered with cover slips and examined by phase contrast and fluorescent microscopy. Fusion was assessed as fluorescent labeling of the RBC plasma membranes. For FIGS. 22–24, fluorescent liposomes were incubated with POPC:cholesterol liposomes and/or RBCs as described in section "L," infra. Panels a,c and e of FIGS. 22–24 are views under phase contrast, whereas panels b,d and f of FIGS. 22–24 are the same fields viewed under fluorescent light.

H. Other Procedures

Phospholipid concentrations were determined by assaying for phosphate using the method of Fiske and Subbarow (*J. Biol. Chem.*, 66:375–400 (1925)). Liposome size distributions were determined by quasi-elastic light scattering (QELS) using a Nicomp model 370 particle sizer.

II. Experimental Findings

A. Influence of BSC on the Polymorphic Phase Properties of an Equimolar Mixture of DOPE and Cholesterol $^{31}$P-NMR was used to examine the effect of bilayer stabilizing component (BSC), in this instance poly-(ethyleneglycol)$_{2000}$ conjugated to DOPE (i.e., DOPE-PEG$_{2000}$), on the phase preference of an equimolar mixture of DOPE and cholesterol (FIG. 1). In the absence of BSC, the mixture adopted an inverse hexagonal phase (H$_{II}$) at 20° C. as determined from the characteristic $^{31}$P-NMR lineshape with a low field peak and high field shoulder (Cullis and deKruijff, *Biochim. Blophys. Acta* 559:399–420 (1979)). As the amount of BSC in the mixture was increased, the peak corresponding to H$_{II}$ phase phospholipid disappeared and a high field peak with a low field shoulder, characteristic of bilayer phase phospholipid (Cullis and deKruijff, supra, 1979) appeared. When DOPE-PEG$_{2000}$ was present at 20 mol % of phospholipid, the mixture was almost exclusively bilayer with no evidence of H$_{II}$, phase lipid.

In addition to the peaks corresponding to H$_{II}$ phase and bilayer phase, a third peak indicative of isotropic motional averaging was observed in the presence of BSC (FIG. 1). The size of the isotropic signal varied with the amount of BSC present and, as shown in subsequent Figures, the nature of the BSC species. The signal was largest at concentrations of BSC that allowed $H_{II}$ and bilayer phases to co-exist and diminished when either $H_{II}$ or bilayer phase predominated. Such a signal may be produced by a number of phospholipid phases which allow isotropic motional averaging on the NMR timescale, including micellar, small vesicular, cubic and rhombic phase phospholipids.

Figure 2:
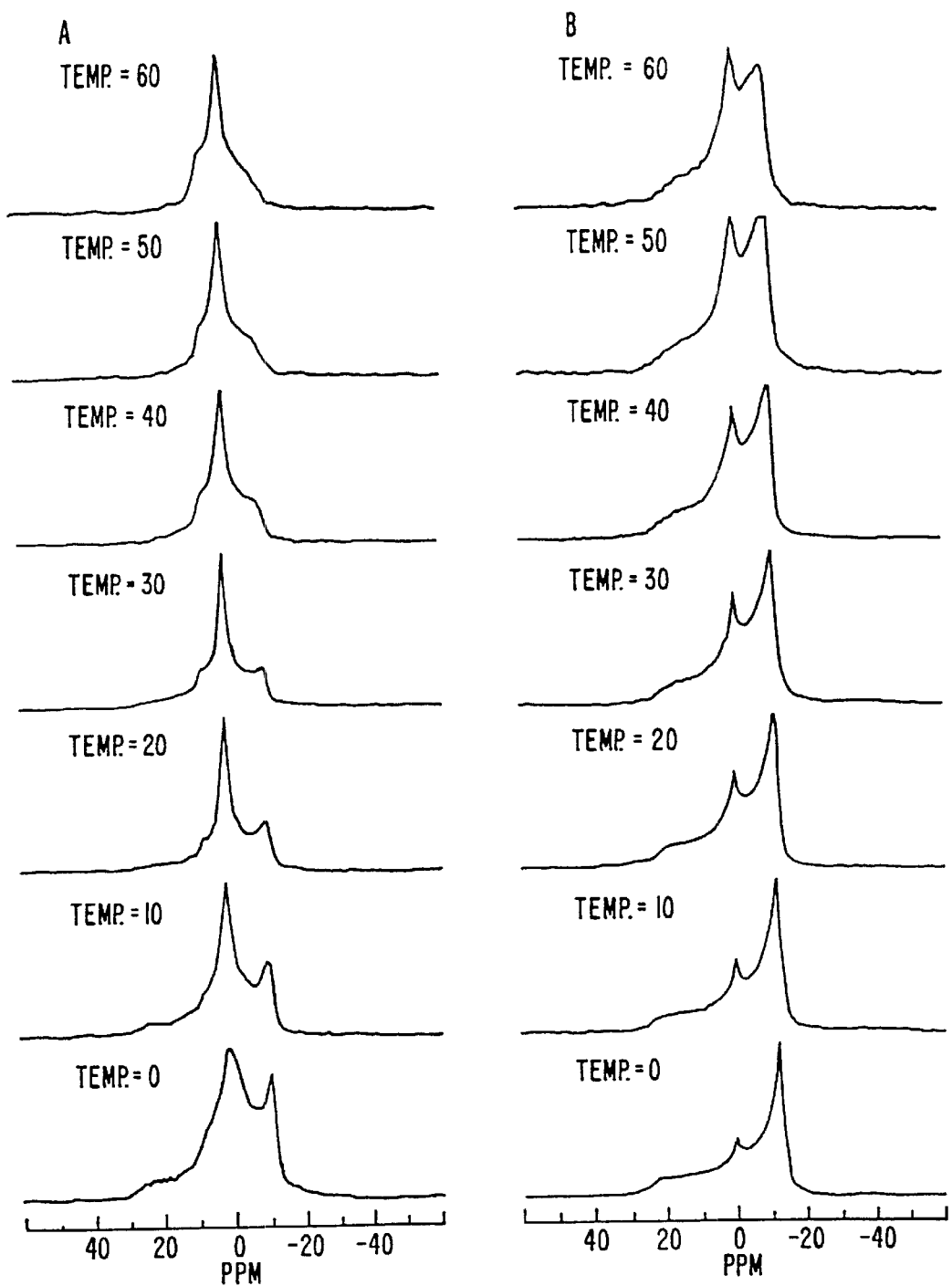
FIG. 2 illustrates the temperature dependence of bilayer stabilization by BSC. Multilamellar vesicles were prepared, as described in the examples, from mixtures of DOPE:cholesterol:DOPE-PEG$_{2000}$ at a ratio of: A, 1:1:0.1; or B, 1:1:0.25. The samples were cooled to 0° C. and $^{31}$p-NMR spectra were determined from 0° C. to 60° C. at 10° C. intervals. The samples were allowed to equilibrate at each temperature for 30 min. prior to data accumulation.

B. The Influence of BSC on the Thermotropic Properties of an Equimolar Mixture of DOPE and Cholesterol FIG. 2 illustrates the effect of temperature on the phase properties of mixtures of DOPE, cholesterol and BSC. When DOPE-PEG$_{2000}$ was present at 9 mol %, there was a large isotropic signal which dominated the spectrum at all temperatures. The predominant, non-isotropic phase at 0° C. was bilayer. However, as the temperature was increased the high field peak diminished and a shoulder corresponding to the low field peak of the $H_{II}$ phase appeared. The apparent bilayer to hexagonal phase transition occurred at 40–50° C., but was almost obscured by the large isotropic signal. DOPE on its own exhibits a sharp transition over an interval of approximately 10° C. (see, FIG. 1 in Tilcock, et al., *Biochemistry* 21:4596–4601 (1982)). The transition in mixtures of DOPE, cholesterol and BSC was slow in comparison with both phases present over a temperature range of almost 40° C. (See also, FIG. 3).

The mixture was stabilized in the bilayer conformation over the same temperature range when the BSC content was increased to 20 mol % (FIG. 2). There was no evidence of phospholipid in the $H_{II}$ phase. In addition, the isotropic signal was markedly reduced at the higher BSC concentration at all temperatures studied. The amount of lipid experiencing isotropic motional averaging increased as the temperature increased for both concentrations of BSC.

C. The Effect of Head Group Size on the Bilayer Stabilizing Properties of BSCs

Figure 3:
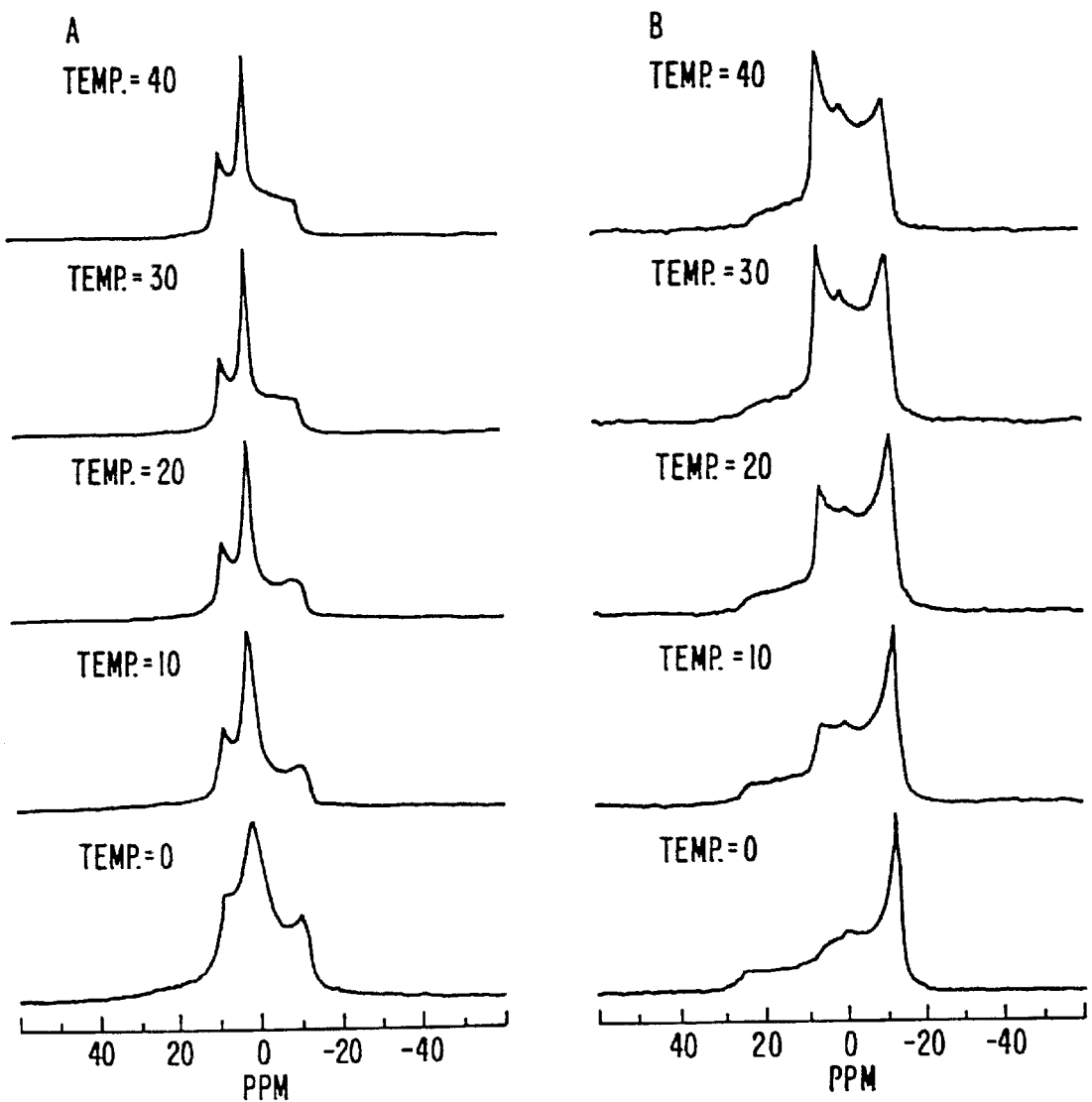
FIG. 3 illustrates the effect of headgroup size on the bilayer stabilizing ability of BSC. Multilamellar vesicles were prepared from either A, DOPE:cholesterol: DOPE-PEG$_{2000}$, 1:1:0.05, or B, DOPE:cholesterol:DOPE-PEG$_{5000}$, 1:1:0.05. Other conditions were the same as for FIG. 2.

The influence of head group size on the bilayer stabilizing properties of BSCs is illustrated in FIG. 3. DOPE-PEG$_{2000}$ at 5 mol % had limited bilayer stabilizing ability. A broad bilayer to $H_{II}$ transition was centered at approximately 10° C., but a large proportion of the lipid adopted non-bilayer phases at all temperatures examined. Increasing the size of the headgroup by using poly-(ethyleneglycol)$_{5000}$ conjugated to DOPE (DOPE-PEG$_{5000}$) in place of DOPE-PEG$_{2000}$, at the same molar fraction, caused a marked increase in bilayer stability. The bilayer to $H_{II}$ transition temperature increased to approximately 30° C. and the isotropic signal was barely discernible. The broadening of the bilayer to $H_{II}$ transition noted above is particularly evident here with $H_{II}$ phase lipid present at 0° C. and bilayer phase lipid present at 40° C.

Figure 4:
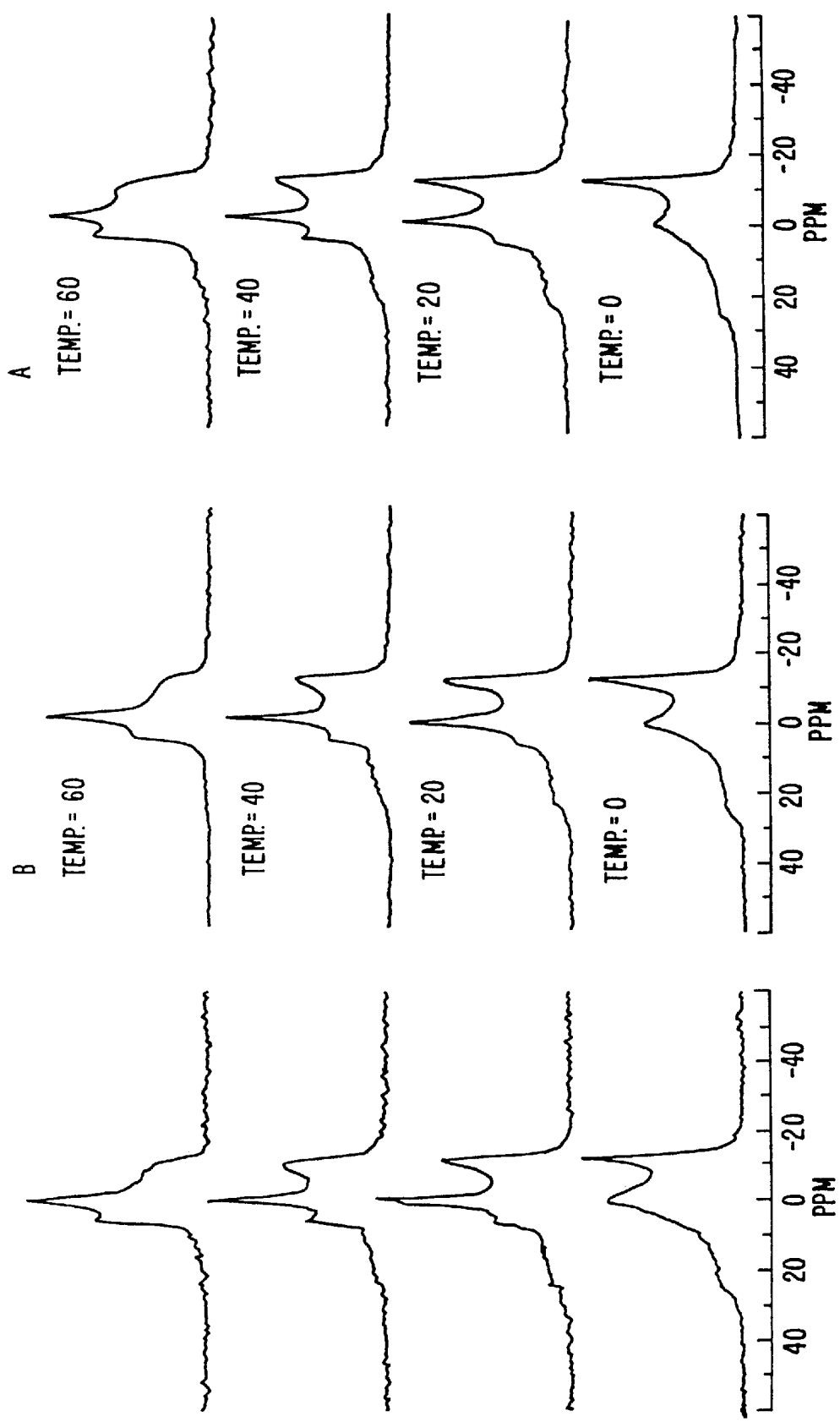
FIG. 4 illustrates the effect of the acyl chain composition on the bilayer stabilizing ability of BSC. Multilamellar vesicles were prepared, as described in the examples, from either A, DOPE:cholesterol:DMPE-PEG$_{2000}$, 1:1:0.1, B, DOPE:cholesterol:DPPE-PEG$_{2000}$, 1:1:0.1, or C, DOPE:cholesterol:DSPE-PEG$_{2000}$, 1:1:0.1. Other conditions were the same as for FIG. 2.

D. The Influence of Acyl Chain Composition on the Bilayer Stabilizing Properties of BSCs The bilayer stabilizing ability of three BSCs differing only in acyl chain composition is shown in FIG. 4. PEG$_{2000}$ conjugated to dimyristoylphosphatidyl-ethanolamine (DMPE-PEG$_{2000}$), dipalmitoylphosphatidylethanolamine (DPPE-PEGM$_{2000}$) or distearoylphosphatidylethanolamine (DSPE-PEG$_{2000}$) showed a similar ability to stabilize an equimolar mixture of DOPE and cholesterol. The bilayer to $H_{II}$ phase transition was raised to approximately 40–50° C. The results are similar to those presented in FIG. 2 which were obtained using a BSC with the same headgroup, but unsaturated acyl groups (DOPE-PEG$_{2000}$ at the same concentration. The size of the isotropic signal varied somewhat with the different BSCs, being smallest with DSPE-PEG$_{2000}$ and largest with DOPE-PEG$_{2000}$ (cf., FIG. 2 and FIG. 4).

E. The Use of PEG-ceramides as Bilayer Stabilizing Components

Figure 5:
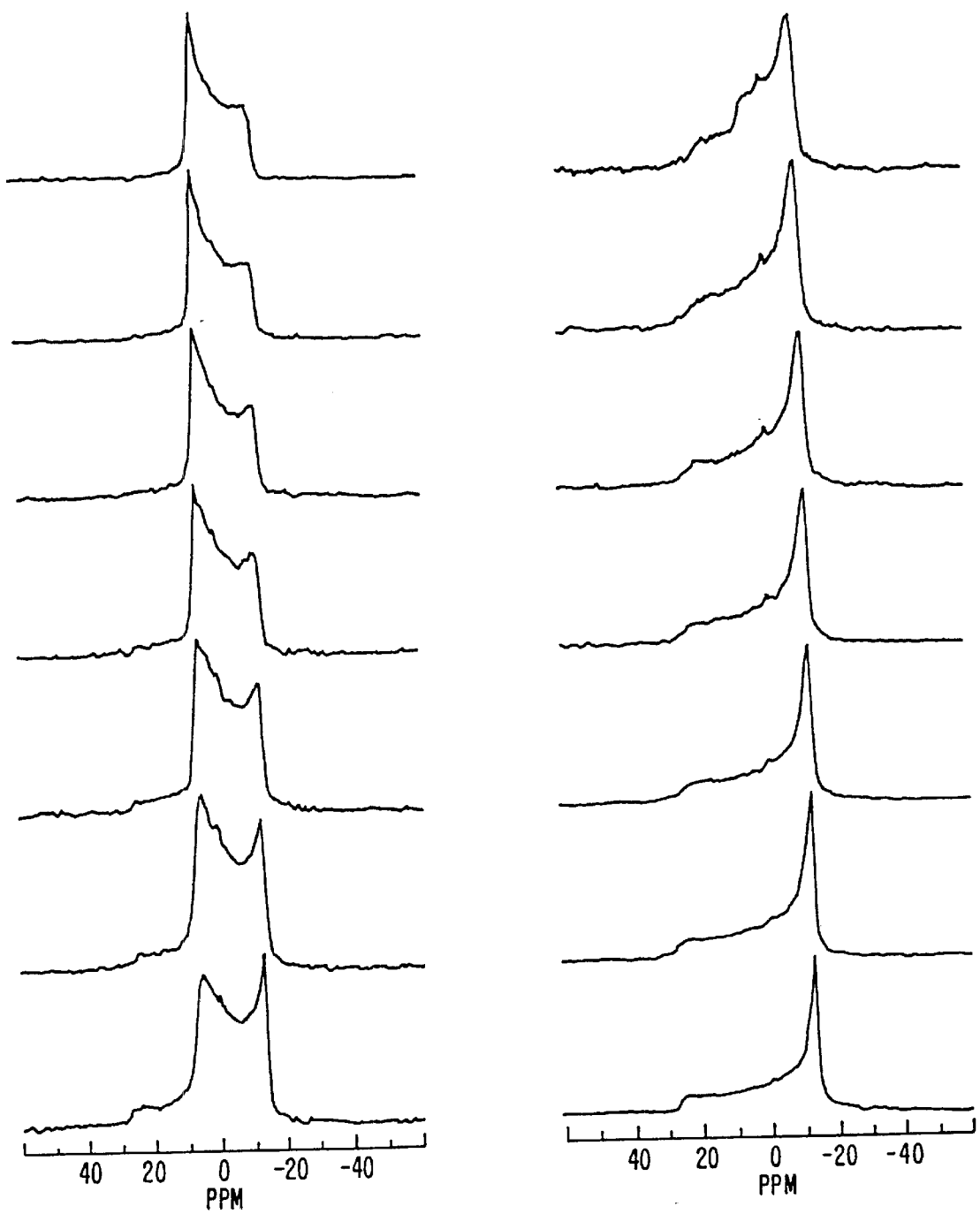
FIG. 5 illustrates the ability of PEG-Ceramide to act as a bilayer stabilizing component. Multilamellar vesicles were prepared, as described in the examples, from DOPE:cholesterol:egg ceramide-PEG$_{2000}$ at a ratio of A, 1:1:0.1 or B, 1:1:0.25. Other conditions were the same as for FIG. 2.

The spectra set forth in FIGS. 1–4 were all obtained using PEG conjugated to phosphatidylethanolamine through a carbamate linkage. In addition, however, the use of ceramide as an alternative anchor for the hydrophilic polymer was examined. PEG$_{2000}$ was conjugated via a succinate linker to egg ceramide. FIG. 5 shows the $^{31}$P-NMR spectra obtained using mixtures of DOPE:cholesterol:egg ceramide-PEG$_{2000}$ (1:1:0.1 and 1:1:0.25) over the temperature range of 0 to 60° C. At the lower molar ratio of PEG-ceramide, both bilayer and $H_{II}$ phase lipid are in evidence at most temperatures. However, at the higher PEG-ceramide molar ratio, the spectra are exclusively bilayer up to 60° C. at which point a low field shoulder corresponding to $H_{II}$ phase lipid is visible. Unlike the spectra obtained using PEG-PEs, there was almost no isotropic signal when PEG-ceramide was used.

F. Freeze-fracture Electron Microscopy

Figure 6:
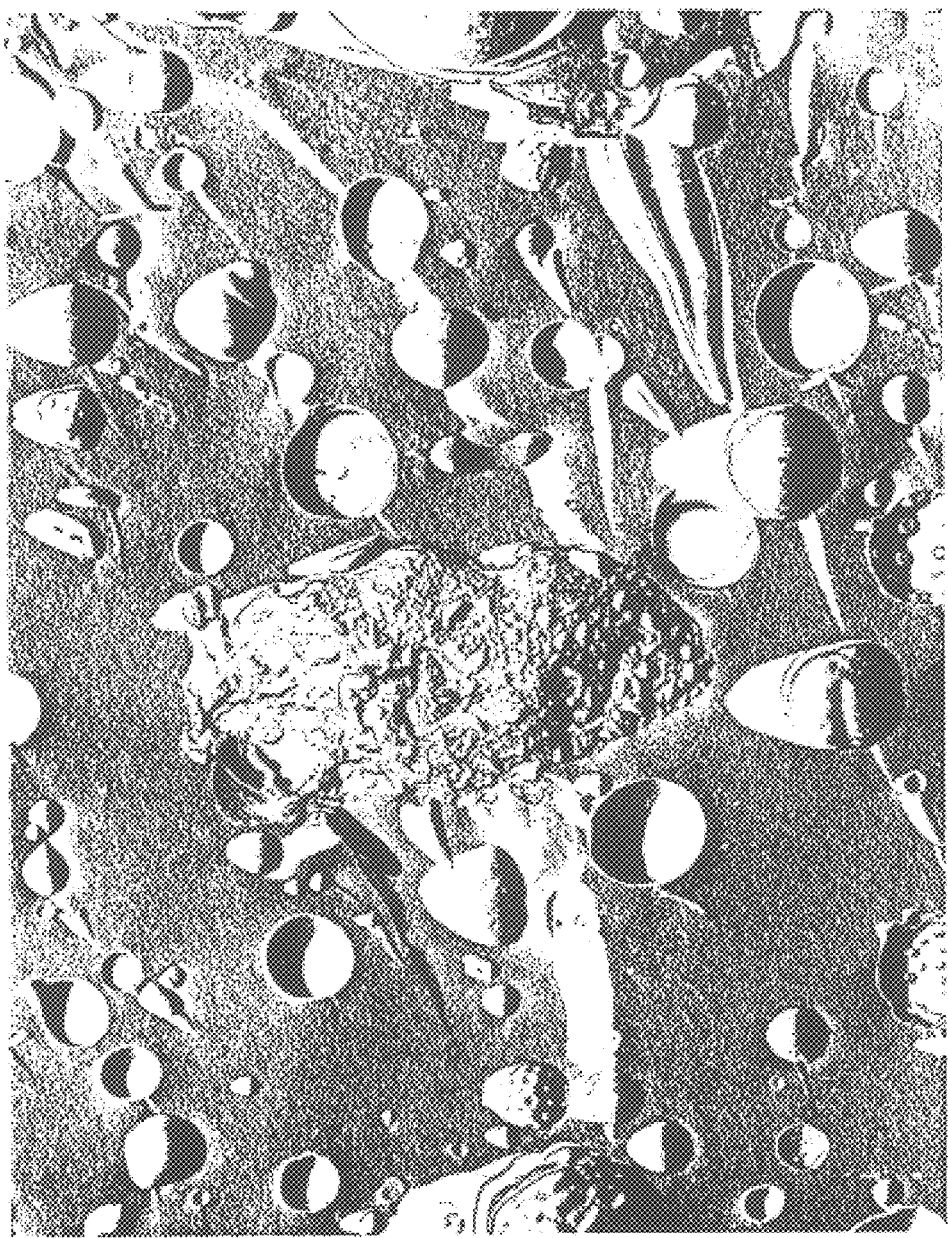
FIG. 6 illustrates the freeze-fracture electron micrograph of MLVs prepared from DOPE:cholesterol:DOPE-PEG$_{2000}$ (1:1:0.1). The samples were prepared as described in the examples. The bar represents 500 nm.

One of the interesting features of several of the NMR spectra was the narrow signal at 0 ppm, indicative of isotropic motional averaging. This signal can arise from a number of phospholipid phases such as micellar, small vesicular, cubic and rhombic phase structures. Freeze-fracture electron microscopy was used to investigate this aspect further. FIG. 6 shows an electron micrograph of MLVs prepared by hydrating a mixture of DOPE:cholesterol:DOPE-PEG$_{2000}$ (1:1:0.1) with HBS at room temperature. This lipid mixture corresponds to the NMR spectra set forth in FIG. 2A which exhibited evidence of bilayer, $H_{II}$ and isotropic phases.

A number of different structures are visible in the micrograph. Much of the lipid is present as large spherical vesicles of 400 to 600 nm in diameter. Many of the vesicles have indentations which appear to be randomly distributed in some vesicles, but organized in straight or curved lines in others. Cusp-like protrusions are also visible on the concave surfaces of some vesicles. These features are commonly referred to as lipidic particles (Verkleij, A. J., *Biochim. Biophys. Acta*, 779:43–92 (1984)) and may represent an intermediate structure formed during fusion of bilayers. These large vesicles would be expected to give rise to a predominately bilayer $^{31}$P-NMR spectrum with a narrow isotropic signal due to the lipidic particles. Similar results have been observed with N-methylated PEs (Gagne, et al., *Biochemistry*, 24:4400–4408 (1985)). A number of smaller vesicles of around 100 nm diameter can also be seen. These vesicles may have been formed spontaneously on hydration, or may have been produced by vesiculization of larger vesicles. These vesicles are sufficiently small for lipid lateral diffusion, or tumbling of the vesicles in suspension, to produce motional averaging on the NMR timescale (Bumell, et al., *Biochim. Biophys. Acta*, 603:63–69 (1980)), giving rise to an isotropic signal (see, FIG. 2A). In the center of FIG. 6 is a large aggregate showing evidence of several different structures. The right side of the aggregate is characterized by what appears to be closely packed lipidic particles. The upper left hand side shows a distinct organization into three-dimensional cubic arrays and the lower left hand region has the appearance of stacked tubes characteristic of lipid adopting the Ha phase (Hope, et al., *J. Elect. Micros. Tech.*, 13:277–287 (1989)). This is consistent with the corresponding $^{31}$P-NMR spectrum.

Figure 7:
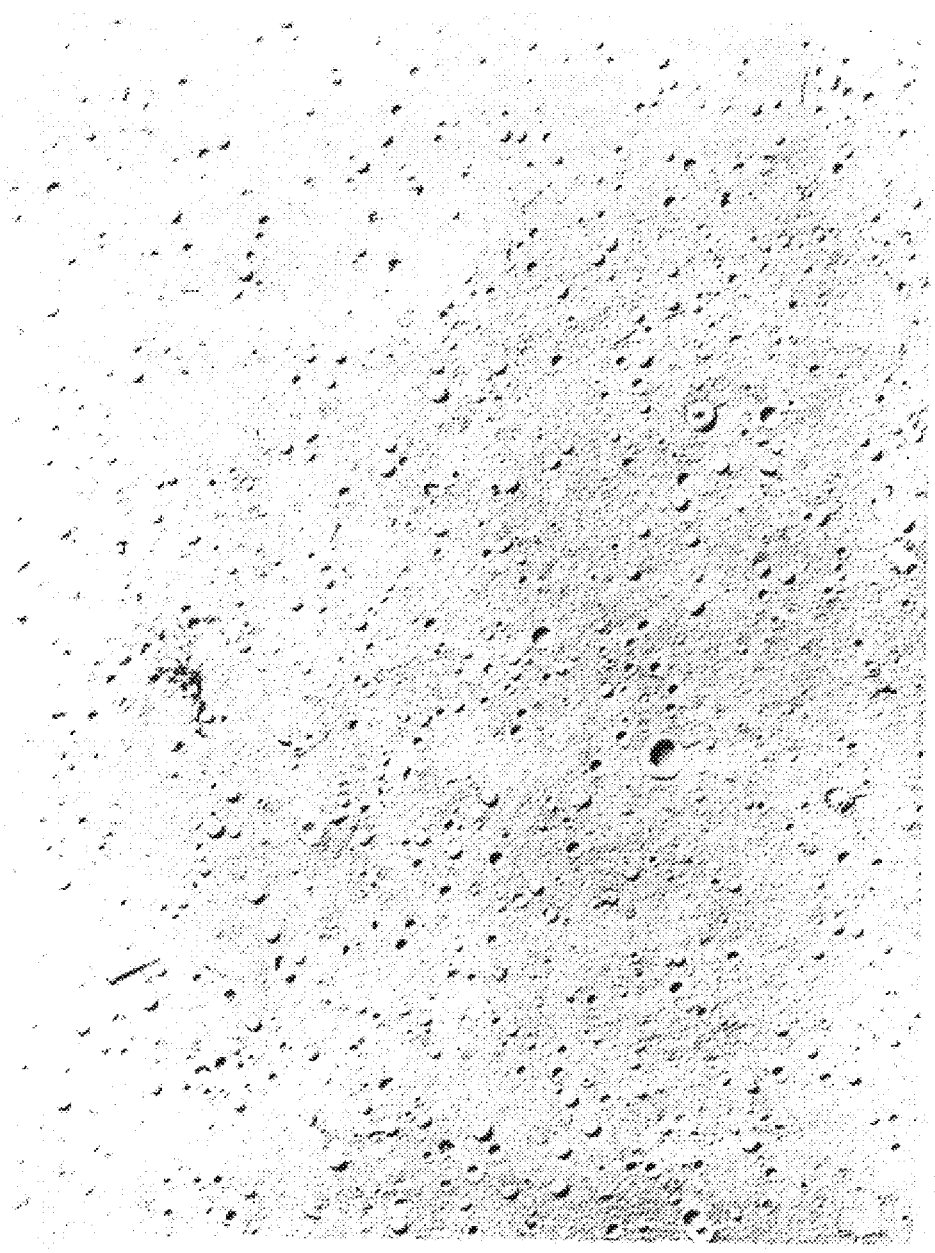
FIG. 7 illustrates the freeze-fracture electron micrograph of LUVs prepared from DOPE:cholesterol:DOPE-PEG$_{2000}$ (1:1:0.1). The samples were prepared as described in the examples. The bar represents 500nm.

FIG. 7 shows the appearance of the same mixture after extrusion through polycarbonate filters of 100 nm pore size to produce LUVS. The lipid is predominately organized into vesicles of approximately 100 nm in diameter. Closer inspection reveals the presence of occasional larger vesicles and some of tubular shape. Overall the fairly uniform size distribution is typical of that obtained when liposomes are produced by extrusion.

Figure 8:
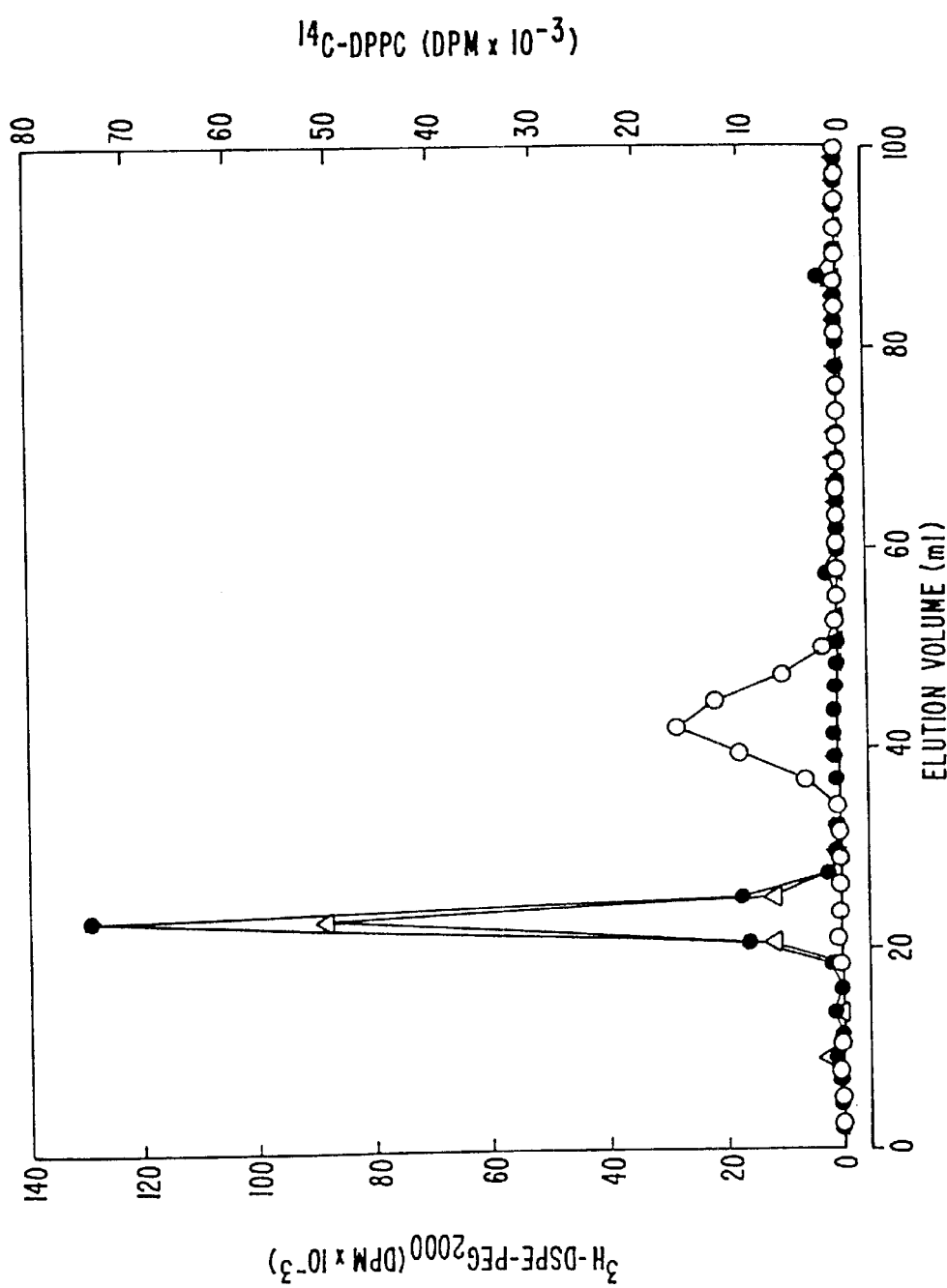
FIG. 8 illustrates the elution profiles of LUVs prepared from DOPE:cholesterol:DSPE-PEG$_{2000}$, and micelles composed of DSPE-PEG$_{2000}$. LUVs were prepared, as described in the examples, from DOPE:cholesterol:DSPE-PEG$_{2000}$ (1:1:0.1) with trace amounts of $^{14}$C-DPPC (Δ) and $^3$H-DSPE-PEG$_{2000}$. (●) They were chromatographed as described in the examples. In a separate experiment, micelles were prepared from DSPE-PEG$_{2000}$ labelled with $^3$H-DSPE-PEG$_{2000}$ (○) and chromatographed on the same Sepharose 4B column.

The presence of lipid micelles is not readily apparent from freeze fracture electron microscopy. Lipid in the micellar phase could, however, contribute to the isotropic signal observed in NMR spectra, and it has previously been shown that PEG-PE conjugates form micelles when hydrated in isolation (Woodle and Lasic, *Biochim. Biophys. Acta*, 113:171–199 (1992)). As such, the presence of micelles was tested by subjecting a suspension of LUVs to molecular sieve chromatography on Sepharose 4B. The liposomes were of the same composition used for the freeze fracture studies above except that DSPE-PEG$_{2000}$ was used in place of DOPE-PEG$_{2000}$, and they contained trace amounts of $^{14}$C-DPPC and $^{3}$H-DSPE-PEG$_{2000}$. The elution profile is shown in FIG. 8. A single peak containing both the phospholipid and PEG-PE conjugate markers was found in the void volume. A control experiment also shown in FIG. 8 demonstrated that micelles, which formed when PEG-PE was hydrated in isolation, were included into the column and would have been clearly resolved if present in the liposomal preparation.

G. Effect of PE-PEG$_{2000}$ On Fusion Of PE:PS LUVs

Figure 9:
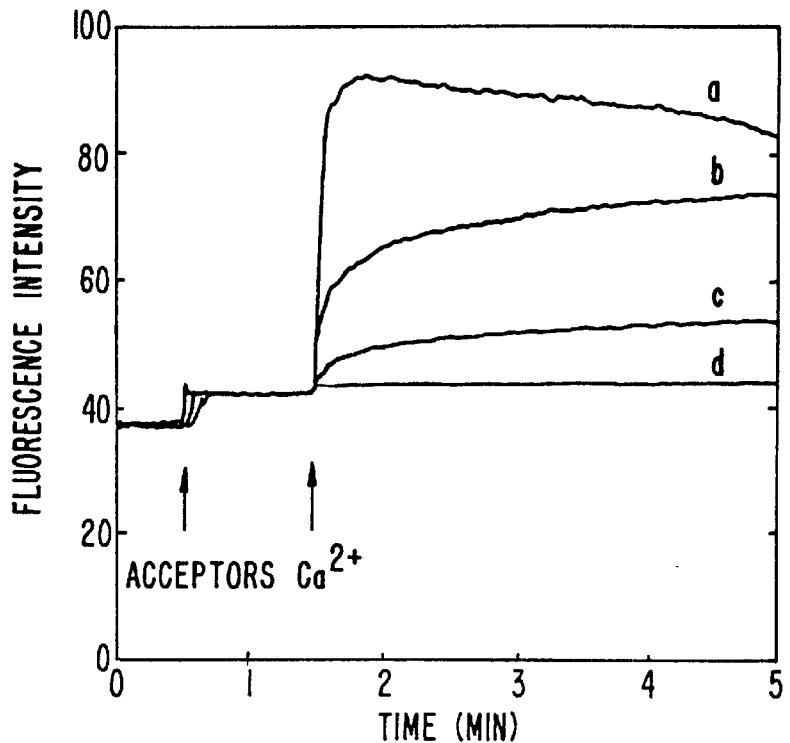
FIG. 9 illustrates the inhibition of fusion by PEG-PE. Liposomes were prepared from equimolar mixtures of DOPE and POPS containing (a) 0; (b) 0.5; (c) 1 or (d) 2 mol % DMPE-PEG$_{2000}$. In addition to the above lipids, labelled liposomes also contained the fluorescent lipids NBD-PE and Rh-PE at 0.5 mol %. Fluorescently labelled liposomes (final concentration 60 1$\mu$M) were incubated at 37° C. for 30s before the addition of a three-fold excess of unlabelled liposomes, followed one minute later by CaCl$_2$ (final concentration 5 mM).

When unlabelled LUVs composed of DOPE:POPS (1:1) were added to fluorescently labelled LUVs there was a small jump in fluorescence intensity due to increased light scattering but no fusion (FIG. 9, trace a). Upon addition of 5 mM Ca$^{2+}$, there was a rapid increase in fluorescence consistent with lipid mixing as a result of membrane fusion. Fusion was complete within a few seconds and was followed by a slow decrease in fluorescence. Inspection of the cuvette revealed the presence of visible aggregates that settled despite stirring, resulting in the observed decrease in fluorescence. When PEG$_{2000}$ conjugated to dimyristoylphosphatidylethanolamine (DMPE-PEG$_{2000}$) was included in both vesicle populations, however, inhibition of fusion was observed. As shown in FIG. 9 (traces b–d), inhibition was dependent on the concentration of DMPE-PEG$_{2000}$ in the vesicles with as little as 2 mol % being sufficient to eliminate Ca$^{2+}$-induced fusion.

H. The Effect of PE-PEG Loss on Fusion

Figure 10:
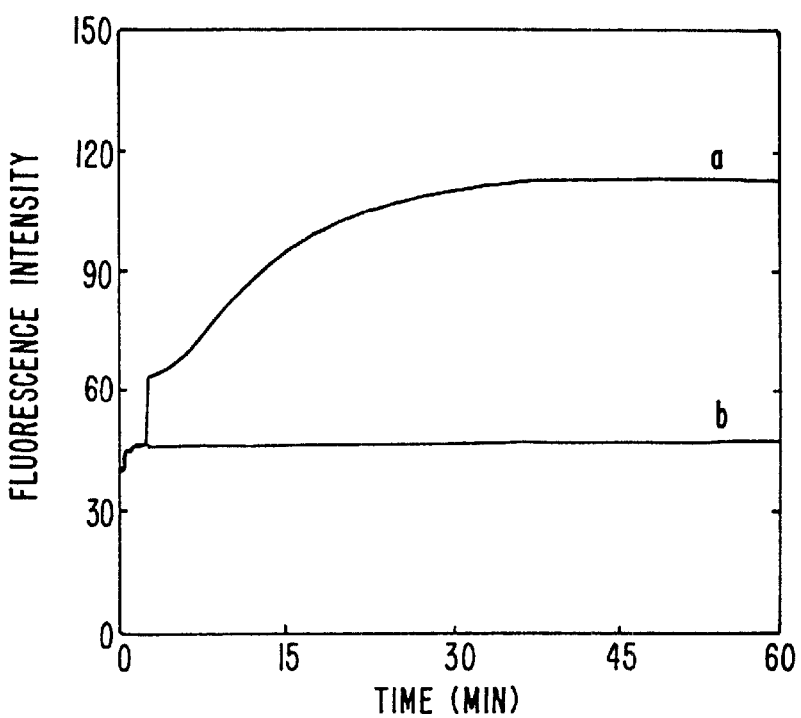
FIG. 10 illustrates the recovery of fusogenic activity after PEG-PE removal. Fusion between fluorescently labelled and unlabelled liposomes containing 2 mol % DMPE-PEG$_{2000}$ was assayed as described under FIG. 9, except that one minute after addition of CaCl$_2$, a 12-fold excess (over labelled vesicles) of POPC liposomes (curve a) or an equivalent volume of buffer (curve b) was added.

Recently, it has been demonstrated that phospholipids conjugated to PEG of molecular weights 750–5,000 Da have enhanced rates of spontaneous transfer between liposomes. The half-time for transfer of these conjugates can vary from minutes to hours and depends on both the size of the PEG group and the nature of the acyl chains which anchor the conjugate in the bilayer. As such, fusion was examined under conditions where the PEG-lipid would be expected to transfer out of the liposomes. Ca$^{2+}$ ions were added to PE:PS liposomes containing 2 mol % DMPE-PEG$_{2000}$, followed by a twelve-fold excess (over labelled vesicles) of 1-paimitoyl-2-oleoyl-phosphatidylcholine (POPC) liposomes as a sink for the PEG-PE. As shown in FIG. 10 (curve a), while fusion was initially blocked by the presence of DMPE-PEG$_{2000}$, the addition of POPC liposomes, which acted as a sink, lead to recovery of full fusogenic activity following a short time lag. The small initial jump in fluorescence intensity that occurred when POPC liposomes were added to PE:PS liposomes resulted from increased light scattering, not fusion. Control experiments demonstrated that no fusion occurred between the PE:PS liposomes and the POPC liposomes (data not shown), and no fusion occurred in the absence of POPC liposomes (FIG. 10, curve b).

Figure 11:
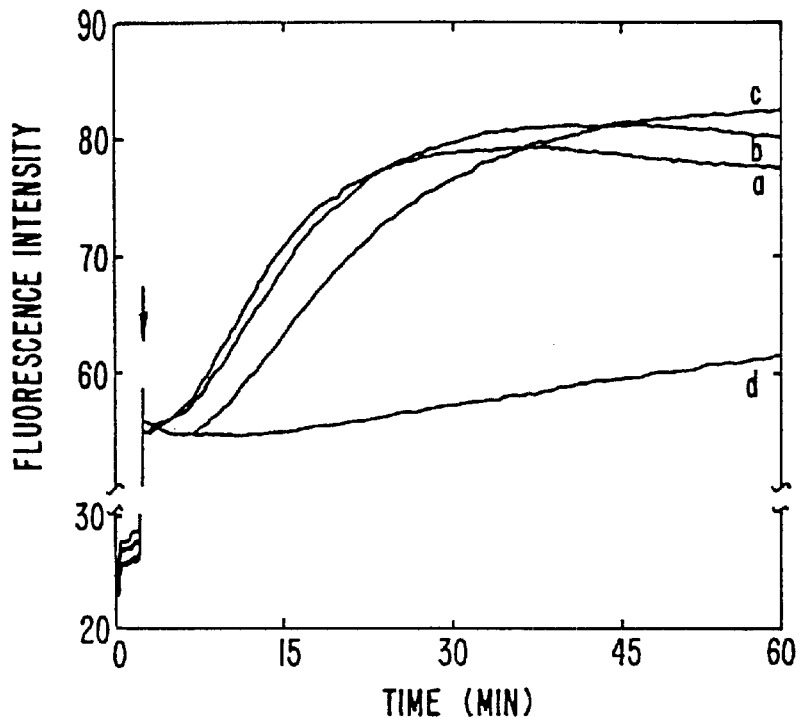
FIG. 11 illustrates the concentration dependence of recovery of fusogenic activity. Fusion between fluorescently labelled and unlabelled liposomes containing (a) 2; (b) 3; (c) 5 or (d) 10 mol % DMPE-PEG$_{2000}$ was assayed as described under FIG. 10, except that POPC liposomes were added as a 36fold excess over labelled vesicles.

To confirm that recovery of fusogenic activity was dependent on removal of the PEG-PE, the influence of initial PEG-lipid concentration on the duration of the lag phase prior to fusion was examined (FIG. 11). Liposomes containing equimolar PE and PS were prepared with 2, 3, 5 or 10 mol % DMPE-PEG$_{2000}$. Fluorescently labelled and unlabelled vesicles were mixed at a ratio of 1:3 and after the addition of 5 mM CaCl$_2$, a 36fold excess (over labelled vesicles) of POPC liposomes was added. As expected, there was an increase in the time delay prior to fusion with increasing PEG-lipid concentration.

I. The Effect of Conjugate Acyl Chain Composition on Fusogenic Activity

Figure 12A:
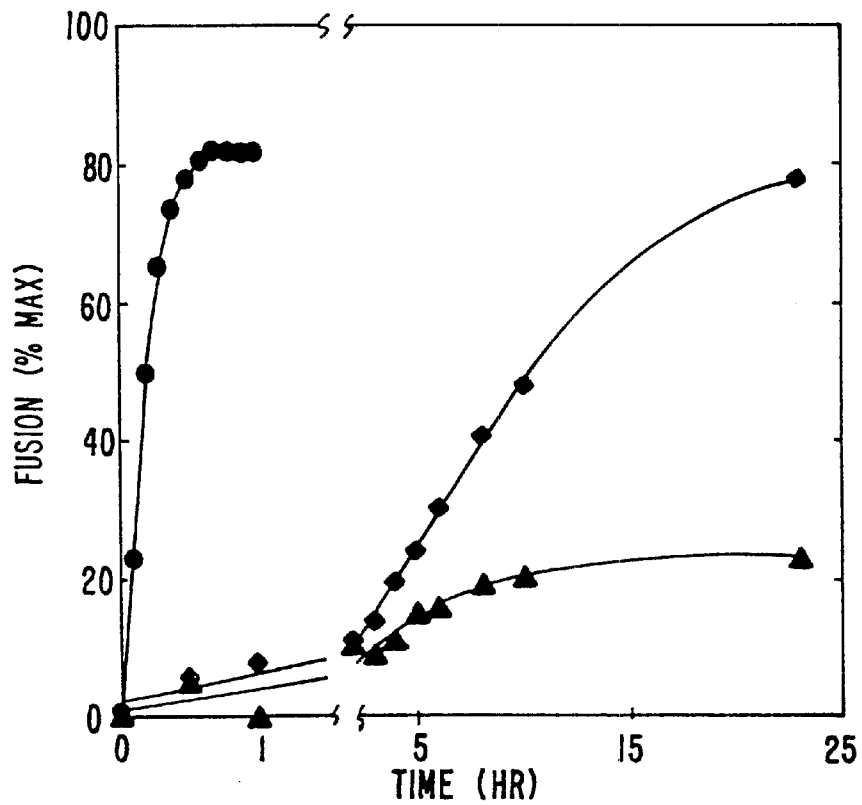
FIGS. 12A and B illustrate programmable fusion. Fusion between fluorescently labelled and unlabelled liposomes containing 2 mol % of the indicated PE-PEG$_{2000}$ was assayed as described under FIG. 10. The % fusion was calculated as described in the examples. (A) DMPP-PEG$_{2000}$ (●); DPPE-PEG$_{2000}$ (♦); DSPE-PEG$_{2000}$ (▼); and (B) DOPE-PEG$_{2000}$ (▼), egg ceramide-PEG$_{2000}$ (▲).

Since fusion is dependent on prior transfer of the PEG-PE out of the liposomes, it was thought that the rate at which fusogenic activity was recovered would depend on the rate of transfer of the PEG-PE. One factor that affects the rate at which a phospholipid transfers from one membrane to another is the length of its acyl chains. As such, the effect of conjugate acyl chain composition on fusogenic activity was investigated. In doing so, the recovery of fusogenic activity of PE:PS LUVs containing 2 mol % DMPE-PEG$_{2000}$ was compared with PE:PS LUVs containing 2 mol % DPPE-PEG$_{2000}$ and 2 mol % DSPE-PEG$_{2000}$ (FIG. 12A). Increasing the length of the acyl chains from 14 to 16 carbons caused a dramatic increase in the lag period before fusion was initiated. Although the same level of fusion occurred using either DMPE-PEG$_{2000}$ or DPPE-PEG$_{2000}$, it was essentially complete in 40 minutes when DMPE-PEG$_{2000}$ was the stabilizer, but took 24 hours when DPPE-PEG$_{2000}$ was used. The implied decrease in rate of transfer (30–40 fold) is consistent with previous measurements of the effect of acyl chain length on rates of spontaneous phospholipid transfer. Increasing the acyl chain length to 18 carbons (DSPE-PEG$_{2000}$, FIG. 12A) extended the lag in fusion even further and, after 24 hours, the level was only 20% of maximum.

Figure 12B:
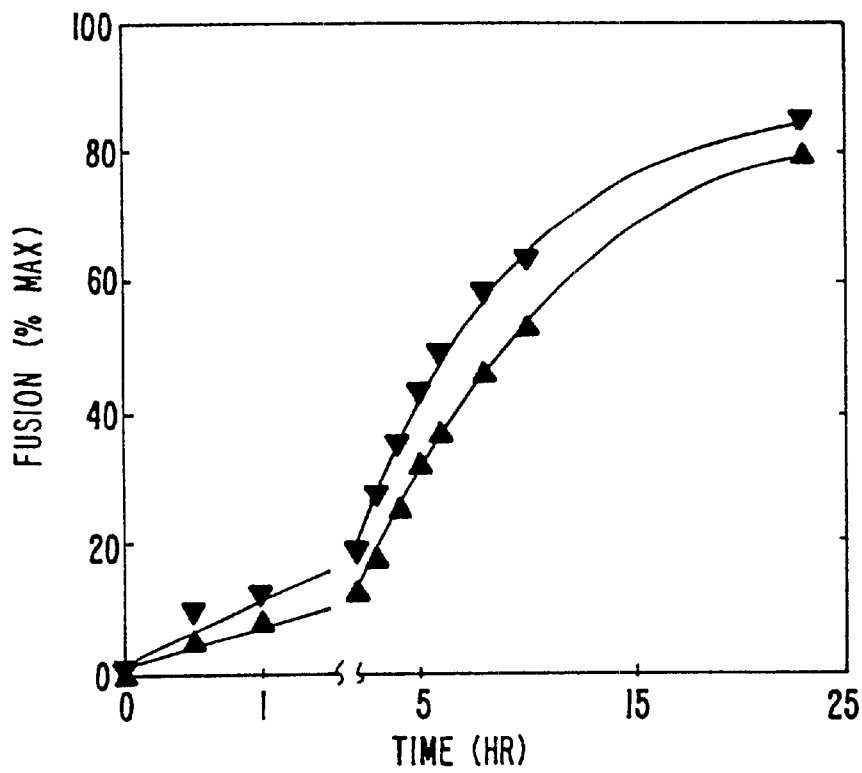

A second factor that affects the rate of spontaneous transfer of phospholipids between bilayers is the degree of saturation or unsaturation of the acyl chains. The rate of fusion of LUVs containing 2 mol % DOPE-PEG$_{2000}$ is shown in FIG. 12B. The presence of a double bond increased the rate of recovery of fusogenic activity in the presence of a sink for the DOPE-PEG$_{2000}$ over that of the corresponding saturated species (DSPE-PEG$_{2000}$, FIG. 12A). The rate of fusion was similar to that seen with DPPE-P$_{2000}$. FIG. 12B also shows the rate of fusion obtained when the neutral PEG-lipid species, egg ceramide-PEG$_{2000}$ was used. The rate was somewhat faster than observed with DPPE-PEG$_{2000}$. Although differences in the interaction of the two lipid anchors with neighboring phospholipids in the bilayer make direct comparison of interbilayer transfer rates and, hence, fusion difficult, it appears that the presence of a negative charge on the conjugate (PE-PEG) is not required for desorption of the conjugate from negatively charged bilayers.

J. Effect of PEG Molecular Weight on Fusogenic Activity

Figure 13A:
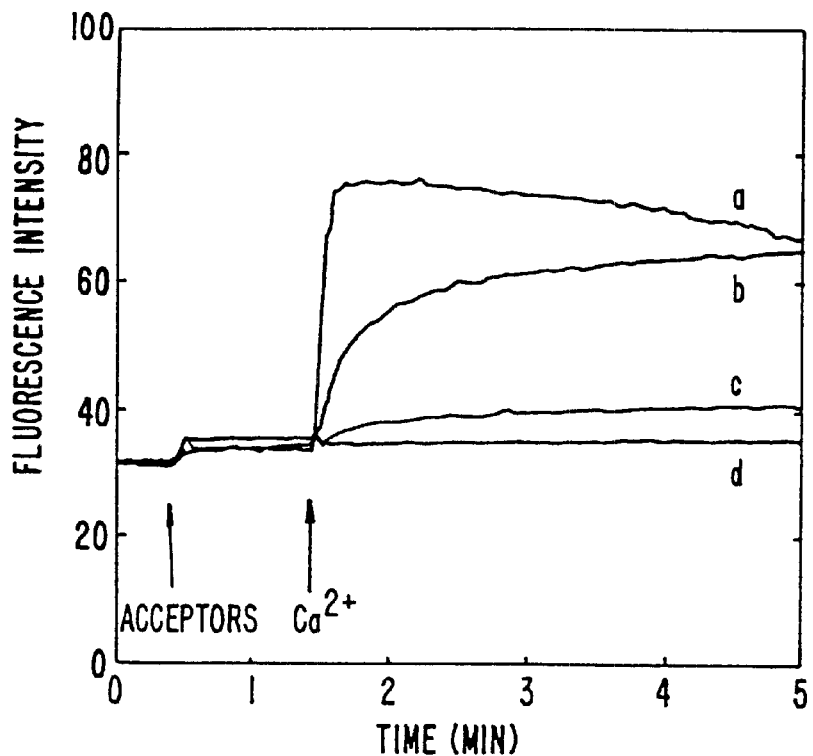
FIGS. 13 A and B illustrate the effect of PEG molecular weight on fusion. (A) Assays were carried out as described in FIG. 9 using liposomes which contained (a) 0; (b) 0.25; (c) 0.5 or (d) 1 mol % DMPE-PEG$_{5000}$; and (B) Assays were performed as described under FIG. 12 using liposomes which contained 1 mol % DMPE-PEG$_{5000}$ (●); DPPE-PEG$_{5000}$ (♦) or DSPE-PEG$_{5000}$ (▼).

The presence of PEG conjugated to the liposome surface results in a steric barrier that inhibits close bilayer apposition and subsequent fusion. The magnitude of the barrier should increase with increasing PEG molecular weight. When DMPE-PEG$_{5000}$ was incorporated into PE:PS (1:1) LUVS, a concentration dependent inhibition of fusion was observed (FIG. 13A). The results are similar to those obtained with DMPE-PEG$_{2000}$ (FIG. 9), except that only 1 mol % DMPE-PEG$_{5000}$ was required to completely inhibit fusion compared to 2 mol % DMPE-PEG$_{2000}$.

Figure 14:
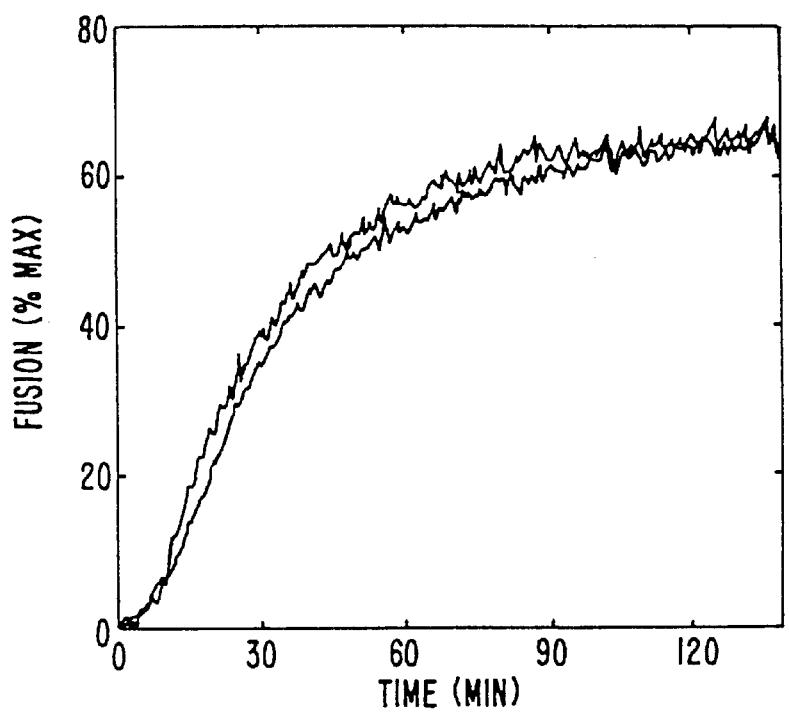
FIG. 14 illustrates the comparison of PEG$_{2000}$ to PEG$_{5000}$ at equal concentration of oxyethylene groups. Liposomes contained either 2 mol % PEG$_{5000}$ (upper curve) or 5 mol % PEG$_{2000}$ (lower curve). Other conditions were as described under FIG. 11.
Figure 13B:
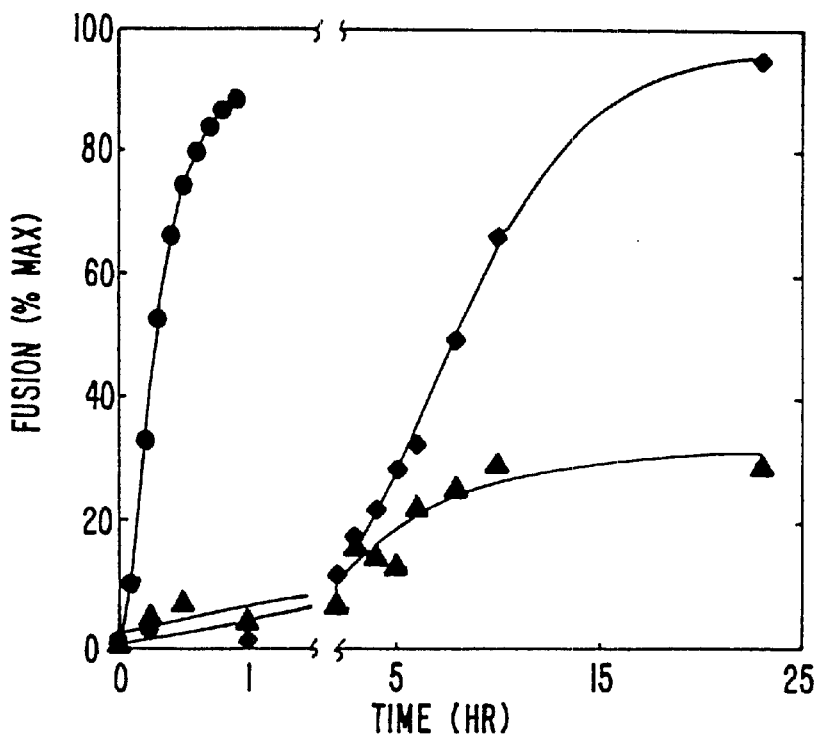

FIG. 13B shows the effect of varying acyl chain composition of the larger PEG-lipid conjugate on fusion. Interestingly, the rates of fusion observed with 1 mol % PE-PEG$_{5000}$ were similar to those with 2 mol % PE-PEG$_{2000}$. The concentrations used were those shown to be sufficient to completely inhibit fusion (cf, FIG. 9 and FIG. 13A). It was thought that the larger PEG group would increase the rate of interbilayer transfer of the conjugate and, hence, the rate of fusion. However, this was not the case. To examine this aspect further, the rates of fusion under conditions where the initial surface density of ethylene glycol groups was similar were compared. FIG. 14 shows the fusion of PE:PS (1:1) LUVs containing 5 mol % DMPE-PEG$_{2000}$ or 2 mol % DMPE-PEG$_{5000}$ after addition of a sink for the PEG-lipid. The rates observed were very similar suggesting that factors other than loss of the steric barrier as a direct result of interbilayer transfer of the conjugate were involved.

Figure 15:
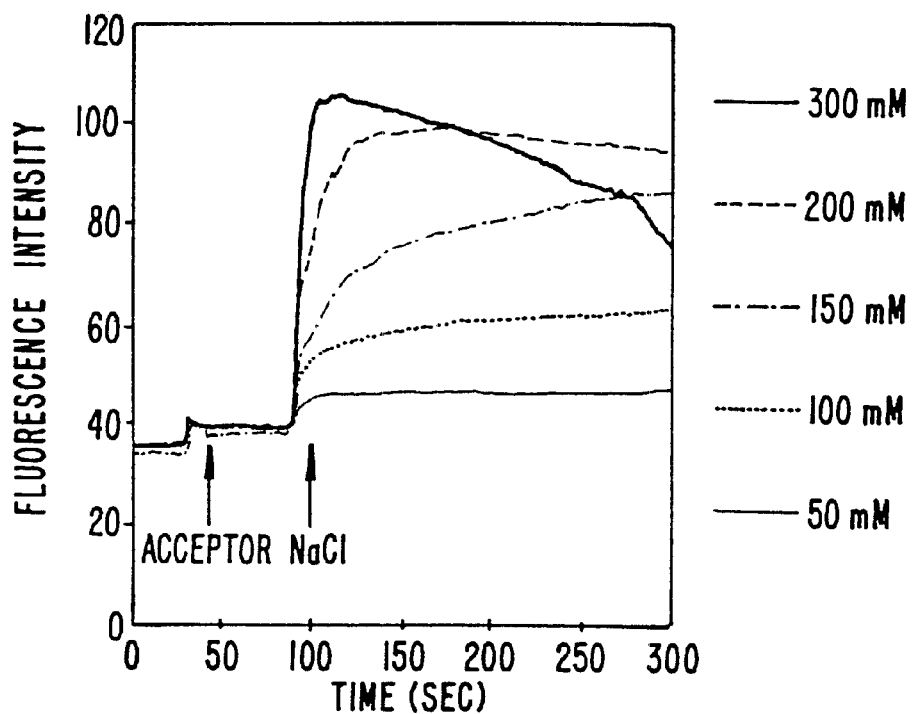
FIG. 15 illustrates the effect of salt concentration on fusion of DOPE:DODAC Liposomes. Liposomes were prepared from DOPE:DODAC (85:15). Donor liposomes also contained the fluorescent lipids, NBD-PE and Rh-PE at 0.5 mol %. Donor liposomes (final concentration 60 μM) were incubated at 37° C. for 30s before the addition of a three-fold excess of unlabelled acceptor liposomes followed 1 min later by NaCl to give the indicated final concentration.

K. Programmable Fusogenic Liposomes Comprising DOPE:cholesterol: DODAC:ceramides Fluorescently labelled liposomes were prepared in distilled water from a mixture of DOPE and N,N-dioleoyl-N, N-dimethylammonium chloride (DODAC) at a molar ratio of 85:15. A three-fold excess of acceptor liposomes of the same composition, but containing no fluorescent probes, was added to labelled liposomes and fusion was initiated after 60s by the addition of NaCl (FIG. 15). Fusion was highly dependent on ionic strength. Little fusion was observed at 50 mM NaCl, but with increasing salt concentration, the rate and extent of fusion increased dramatically. At 300 mM NaCl fusion was so extensive that visible aggregates occurred and these aggregates could not be maintained in suspension resulting in the apparent decrease in fluorescence seen in FIG. 15 for the 300 mM NaCl curve. Importantly, substantial fusion was observed at physiological salt concentration (150 mM).

Figure 16:
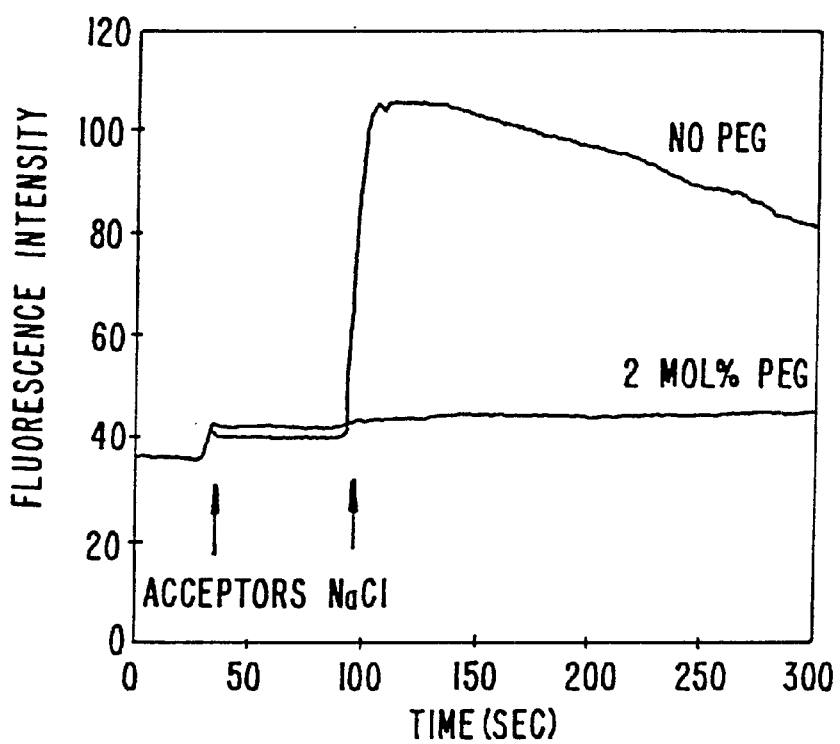
FIG. 16 illustrates the inhibition of fusion of DOPE:DODAC liposomes by PEG-PE. Liposomes were prepared from either DOPE:DODAC (85:15) or DOPE:DODAC:DMPE-PEG$_{2000}$ (83:15:2). Fusion was assayed as described under FIG. 1 using 300 mM NaCl.

As described above, the inclusion of 2 mol % PEG-lipid in PE:PS liposomes is sufficient to inhibit Ca$^{2+}$-induced fusion. When 2 mol % DMPE-PEG$_{2000}$ was included in DOPE:DODAC liposomes (DOPE:DODAC:DMPE-PEG$_{2000}$, 83:15:2), the same inhibitory effect was observed (FIG. 16). However, unlike the PE:PS system, when these liposomes were incubated for 1 hr in the presence of a large excess of POPC liposomes, which acted as a sink for the PEG-PE, little, if any, fusion was observed. Since PEG-PEs are negatively charged the complementary charge, interaction with DODAC likely results in a dramatic decrease in the rate of transfer out of the bilayer.

Figure 17:
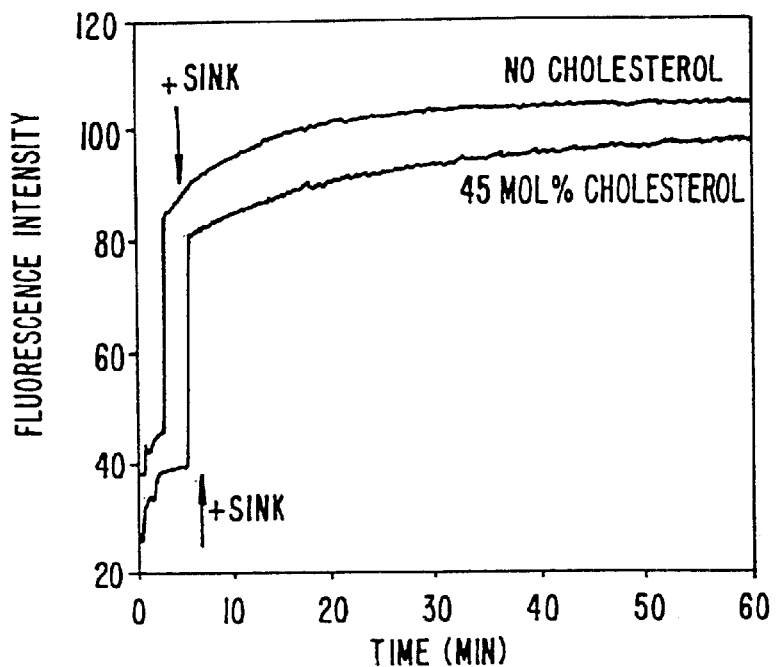
FIG. 17 illustrates the recovery fusogenic activity after PEG removal. Liposomes were prepared from either DOPE:DODAC:ceramide(C8:0)-PEG$_{2000}$, 83:15:2 or DOPE:cholesterol:ceramide(C8:0)-PEG$_{2000}$, 38:45:15:2. Fusion was assayed as described under FIG. 2 except that at the indicated times a 30 fold excess (over donors) of liposomes composed of POPC or POPC:cholesterol (55:45) was added.

As an alternative bilayer stabilizing component, therefore, the ability of a neutral PEG-lipid species, i.e., PEG-ceramide, to inhibit fusion in this system was examined. PEG-ceramides have similar bilayer stabilizing properties to PEG-PEs. For these studies, PEG$_{2000}$ was conjugated to ceramides of various fatty amide chain lengths through a succinate linker. Liposomes prepared from DOPE:DODAC: (C8:0) ceramide-PEG$_{2000}$ (83:15:2) did not fuse in the presence of 300 mM NaCl. However, when an excess of POPC liposomes was added, fusion occurred fairly rapidly (FIG. 17). Similar results were observed when cholesterol was incorporated into the liposomes (DOPE:cholesterol:DODAC:(C8:0) ceramide-PEG$_{2000}$, 38:45:15:2), although the rate of fusion was slower than with cholesterol-free liposomes (FIG. 17).

Figure 18:
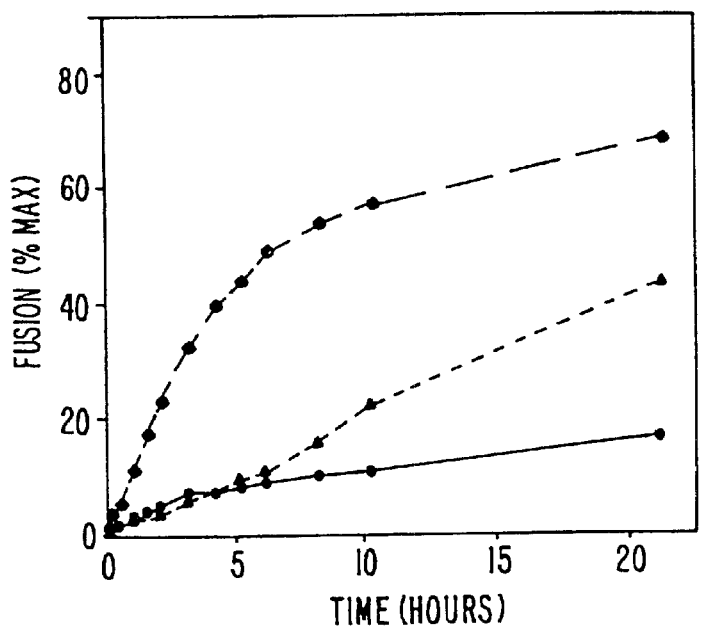
FIG. 18 illustrates the effect of the lipid anchor on the rate of PEG-lipid removal. Fluorescently labelled and unlabelled liposomes were prepared from DOPE:DODAC:PEG-lipid, 83:15:2, using DMPE-PEG$_{2000}$ (●), ceramide(egg)-PEG$_{2000}$ or (C14:0) ceramide-PEG$_{2000}$ (♦). Labelled liposomes were mixed with a 3 fold excess of unlabelled liposomes and 300 mM NaCl in a cuvette in a dark water bath at 37° C. At zero time a 13-fold excess (over labelled vesicles) of POPC liposomes was added and the fluorescence intensity was measured at the indicated times. At the end of the assay Triton X-100 (0.5% final) was added to eliminate energy transfer and the % fusion was calculated from the change in efficiency of energy transfer. Maximum fusion was calculated from a standard curve of energy transfer efficiency against the molar fraction of Rh-PE in the membrane assuming complete mixing of labelled and unlabelled liposomes.

To determine if the rate of fusion in this system can be controlled, the chain lengths of the fatty amide groups of the PEG-ceramides were varied. Using a (C14:0) ceramide-PEG$_{2000}$, 50% maximal fusion was observed after approximately 6 hr (FIG. 18). This was a dramatic increase over the rate with (C8:0) ceramide-PEG$_{2000}$ shown in FIG. 18, where maximal fusion was achieved in about 40 minutes. The time for 50% maximal fusion was increased to over 20 hr when egg ceramide-PEG$_{2000}$ was used. Ceramides derived from egg have a fatty amide chain length of predominantly 16:0 (approximately 78%), with small amounts of longer saturated chains. FIG. 18 also shows an extended time course with DMPE-PEG$_{2000}$. The limited extent of fusion (<20% of maximum at 21 hr) shows the dramatic effect that charge interaction can have on PEG-lipid transfer rates.

Figure 19:
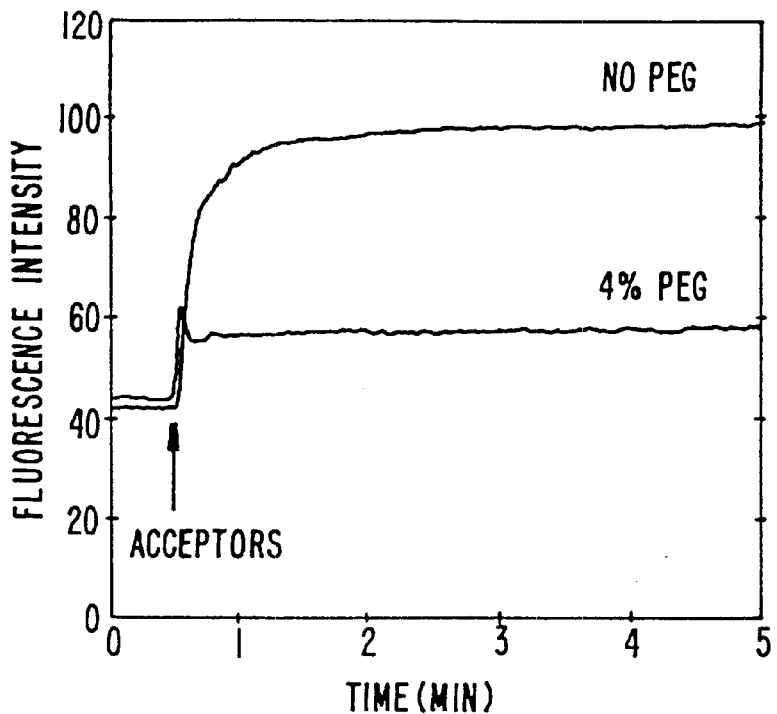
FIG. 19 illustrates the inhibition of fusion between DOPE:cholesterol:DODAC liposomes and anionic liposomes by PEG-ceramide. Liposomes were prepared from DOPE:cholesterol:DODAC, 40:45:15 (no PEG) or DOPE:cholesterol:DODAC:(C14:0) ceramide-PEG$_{2000}$, 36:45:15:4 (4% PEG). Acceptor liposomes were prepared from DOPE:cholesterol:POPS, 25:45:30. A three-fold excess of acceptors was added to labelled vesicles after 30s and the fluorescence monitored at 517 nm with excitation at 465 nm.

The rationale for using cationic liposomes is that complementary charge interaction with anionic plasma membranes will promote association and fusion of liposomes with cells in vivo. It is important, therefore, to confirm that not only will DOPE:DODAC liposomes fuse with membranes carrying a negative charge, but that incorporation of PEG-lipid conjugates prevents fusion in a programmable manner. This ability is demonstrated in FIG. 19 which shows that liposomes composed of DOPE:cholesterol:DODAC, 40:45:15, fuse with negatively charged liposomes and inclusion of a PEG-lipid conjugate in the cationic liposomes inhibits fusion. Fusion between DOPE:DODAC liposomes could be prevented when 2 mol % PEG-lipid was present in both fluorescently labelled and acceptor liposomes. When PEG-lipid was omitted from the acceptor liposomes, however, its concentration in the labelled vesicles had to be increased to 4–5 mol % to block fusion between cationic and anionic liposomes.

Figure 20:
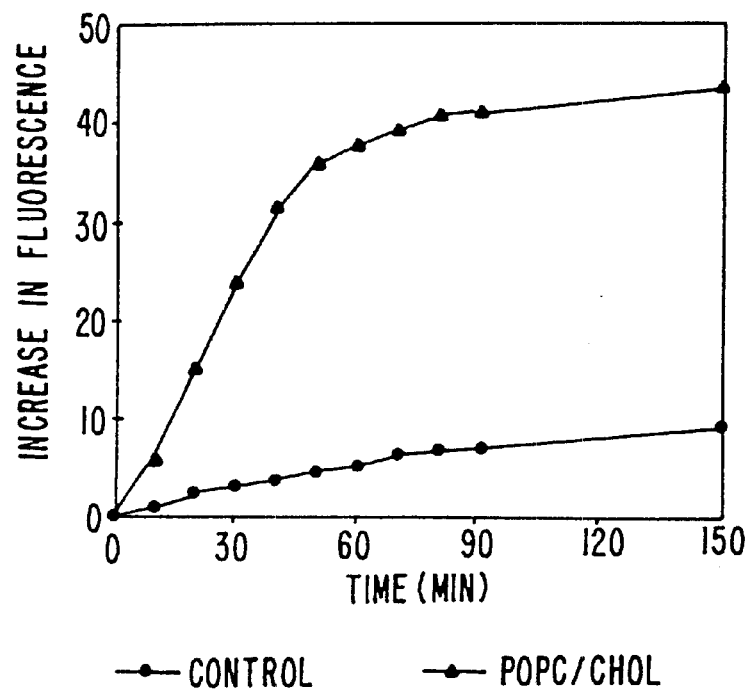
FIG. 20 illustrates the recovery of fusogenic activity upon PEG removal. Donor liposomes (50 μM) were prepared from DOPE:cholesterol:DODAC: (C14:0)ceramide-PEG$_{2000}$, 36:45:15:4 and mixed with acceptor liposomes (150 μM) prepared from DOPE:cholesterol:POPS, 25:45:30. At zero time either 1 mM POPC:cholesterol liposomes (▼) or an equivalent volume of buffer (●) was added. Fluorescence was monitored at 517 nm with excitation at 465nm.

Again, while PEG-lipids can inhibit fusion in this system, under conditions where the PEG-lipid can transfer out of the liposomes, fusogenic activity can be restored. FIG. 20 shows that this is, indeed, the case. Incubation of DOPE:cholesterol: DODAC:(C14:0) ceramide-PEG$_{2000}$ (36:45:15:4) liposomes with PE:PS liposomes, in the presence of excess POPC:cholesterol (55:45) vesicles which act as a sink, results in recovery of fusogenic activity. In the absence of a sink, a slow rate of fusion is observed, indicating that a higher concentration of PEG-lipid is required to completely prevent fusion over longer periods.

Figure 21:
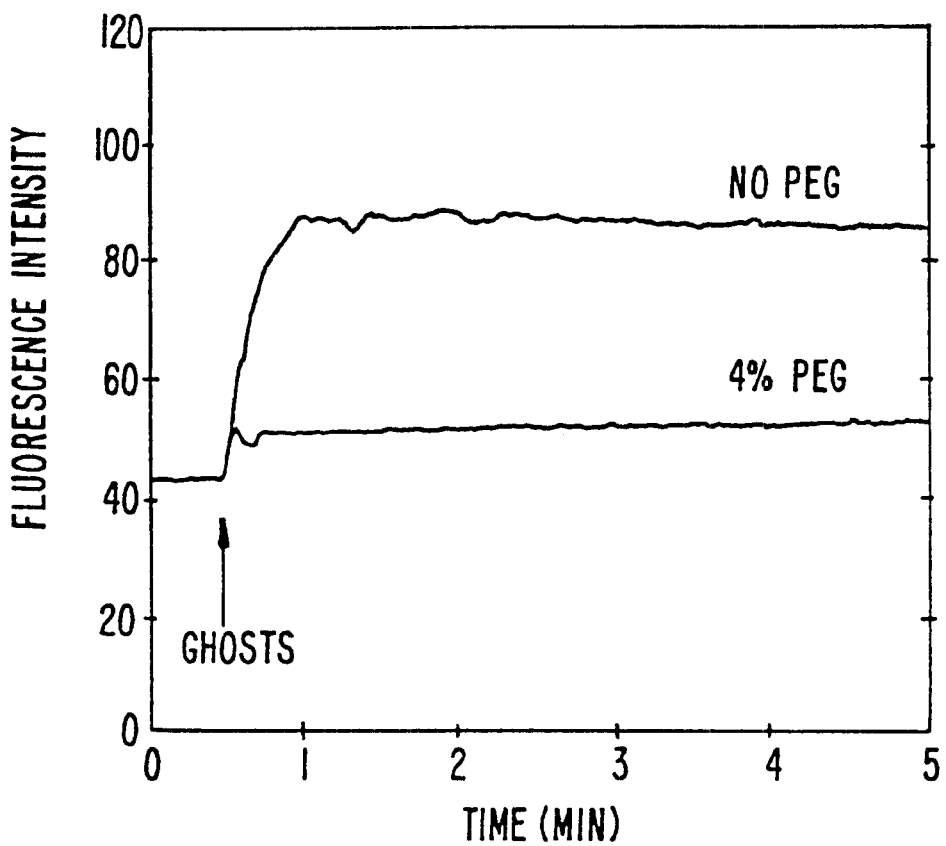
FIG. 21 illustrates the inhibition of fusion between DOPE:cholesterol:DODAC liposomes and erythrocyte ghosts by, PEG-ceramide. Liposomes were prepared from DOPE:cholesterol:DODAC, 40:45:15 (no PEG) or DOPE:cholesterol:DODAC:(C$_{14:0}$)ceramide-PEG$_{2000}$, 36:45:15:4 (4% PEG). Ghosts (50 μM phospholipid) were added to donors (50 μM total lipid) after 30s and the fluorescence monitored at 517 nm with excitation at 465 nm.
Figure 22A:
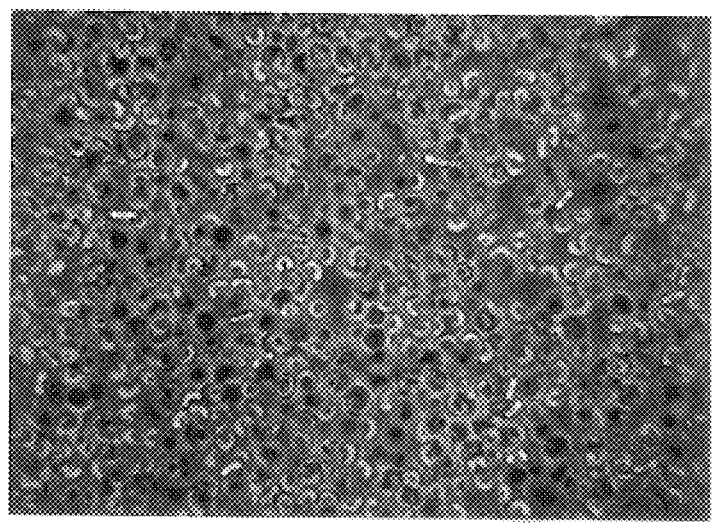
FIGS. 22A–E illustrate the fusion of fluorescent liposomes composed of DOPE:cholesterol:DODAC (40:45:15) or DOPE:cholesterol:DODAC:PEG-ceramide (35:45:15:5). LUVs composed of DOPE:cholesterol:DODAC (40:45:15) fused with RBCs (panels a and b); incorporation of PEG-ceramide (C8:0) into the LUVs at 5 mol % blocked fusion (panels c and d); however, when an exogenous sink for the PEG-ceramide was included, fusogenic activity was recovered within minutes (panels e and f). Panels a,c and e are views under phase contrast, and panels b,d and f are the same fields view under fluorescent light.
Figure 22B:
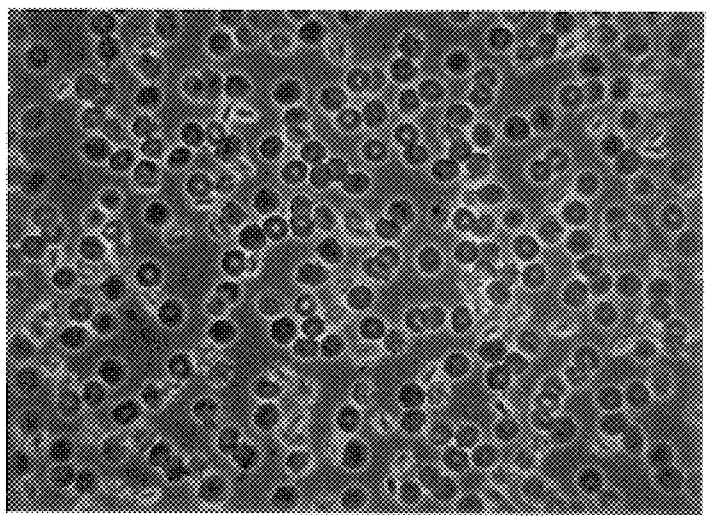
Figure 22C:
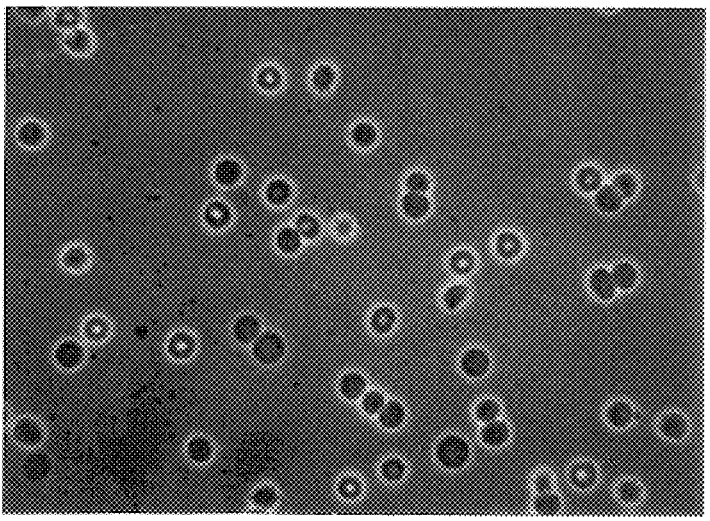
Figure 22D:
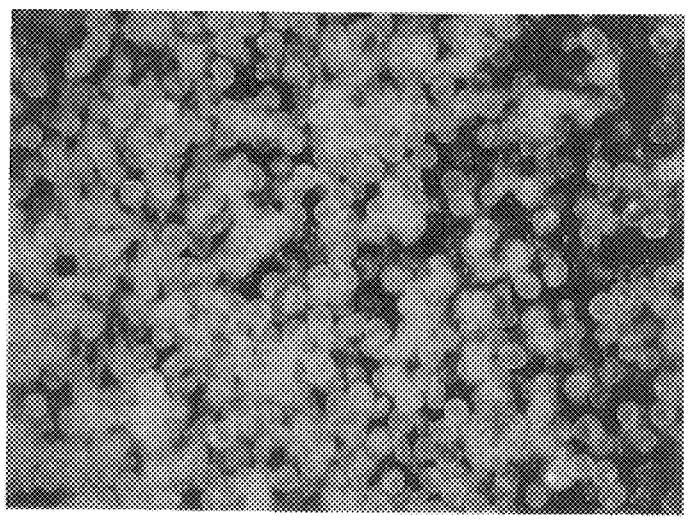
Figure 22E:
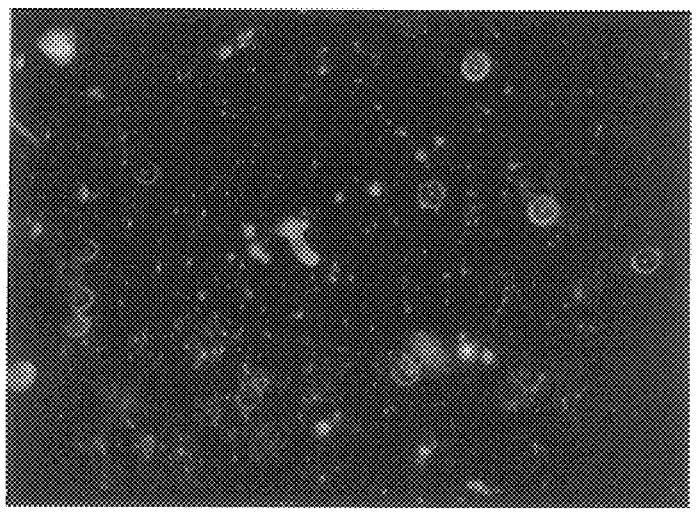
Figure 22F:
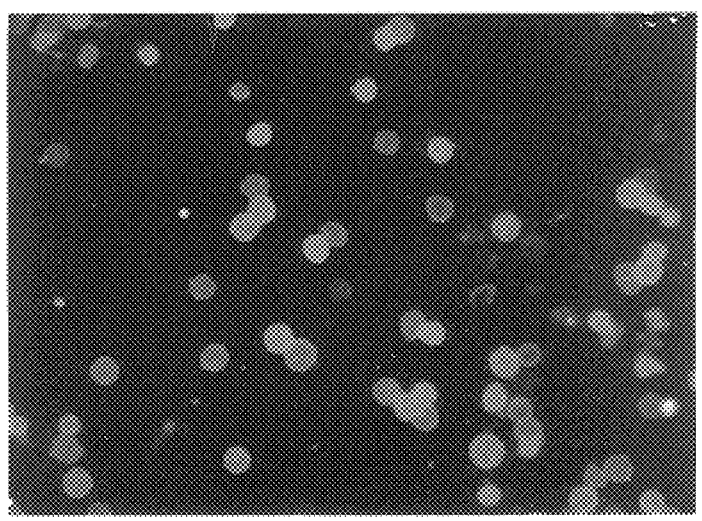
Figure 23A:
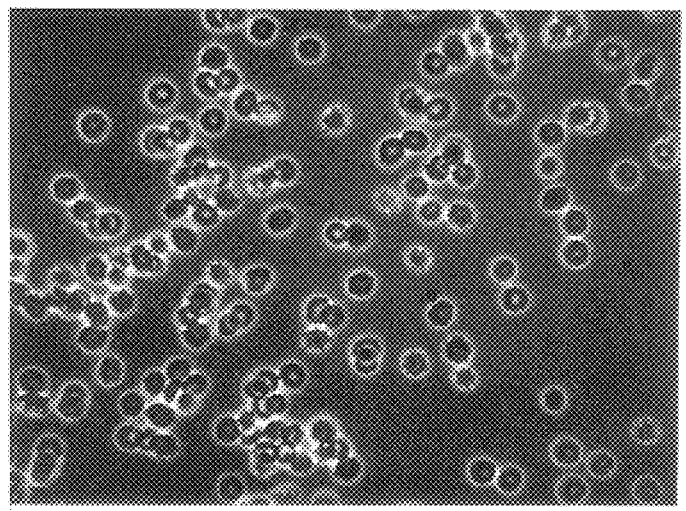
FIGS. 23E–F illustrate the results when PEG-ceramides with longer fatty amide chains (C14:0) are used and the liposomes are pre-incubation with an exogenous sink prior to the addition of the RBCs. No fusion was observed after pre-incubation of the fusogenic LUVs with the sink for five minutes prior to addition of RBC (panels a and b); after a 1 hour pre-incubation, some fusion with RBCs was observed (panels c and d); however, with longer incubations times (2 hours), the pattern of fluorescent labeling changed and extensive punctate fluorescence was observed (panels e and f). Panels a,c and e are views under phase contrast, and panels b,d and f are the same fields view under fluorescent light.
Figure 23B:
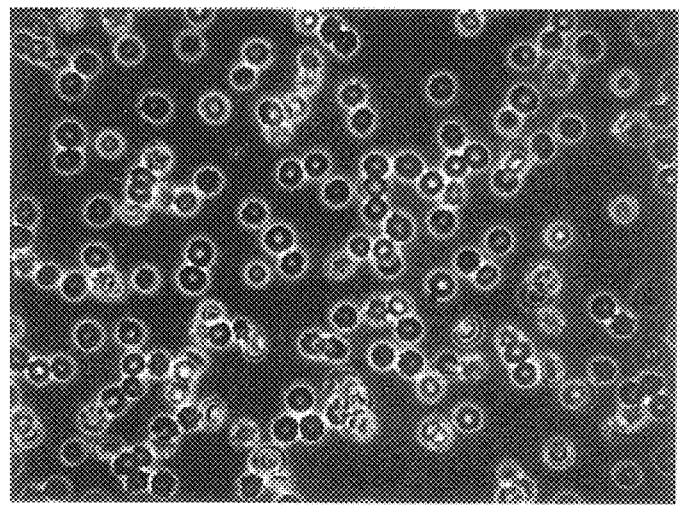
Figure 23C:
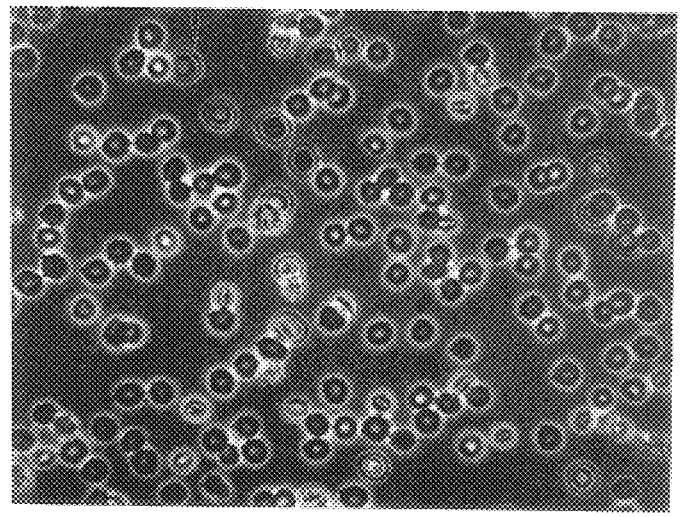
Figure 23D:
Figure 23E:
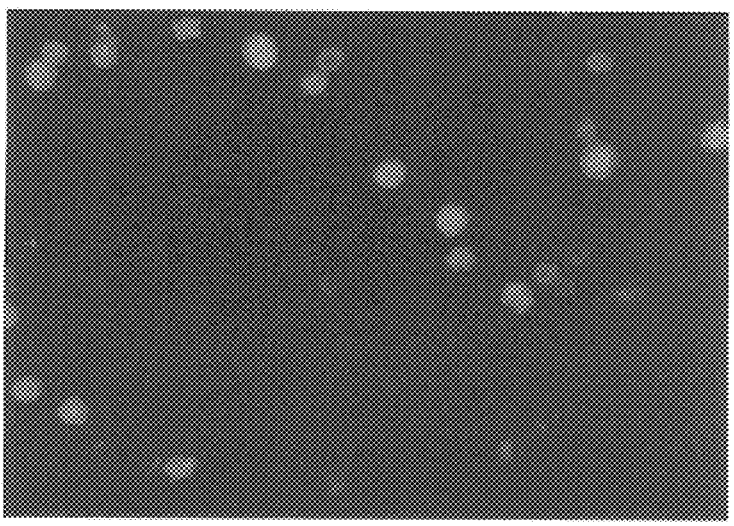
Figure 23F:
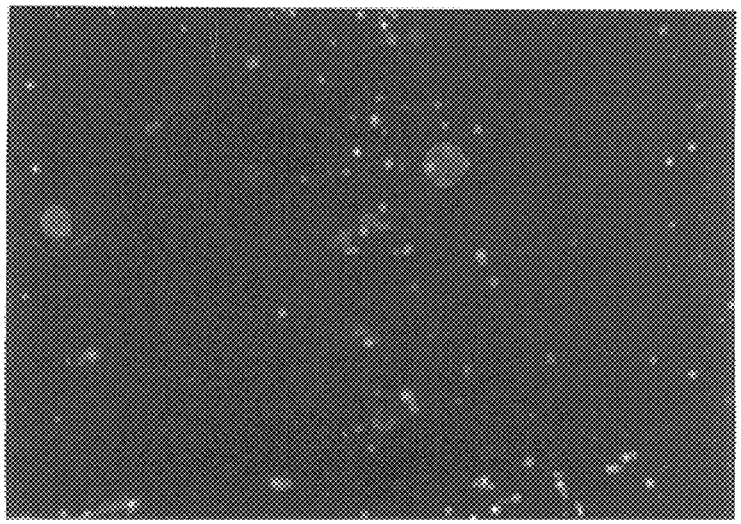
Figure 24A:
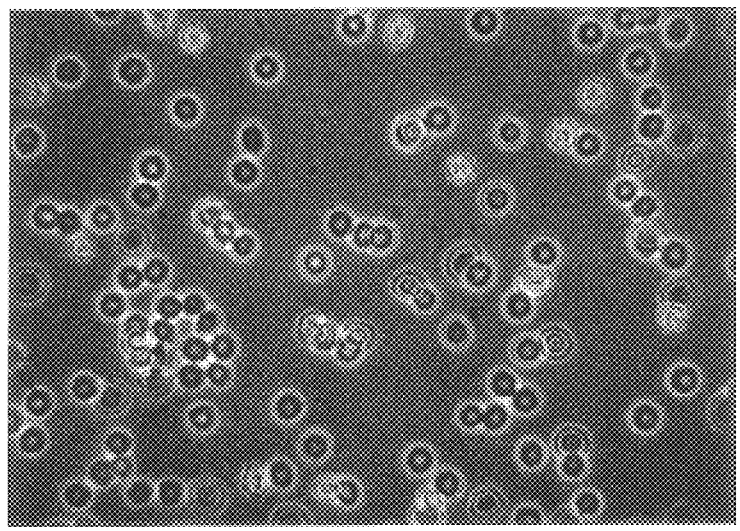
FIGS. 24A–F illustrate the results when PEG-ceramides with longer fatty amide chains (C20:0) are used and the liposomes are preincubation with an exogenous sink prior to the addition of the RBCs. No fusion was observed after pre-incubation of the LUVs with the sink for five minutes (panels a and b), 1 hour (panels c and d) or 2 hours (panels e and f). Panels a, c and e are views under phase contrast, and panels b,d and f are the same fields view under fluorescent light.
Figure 24B:
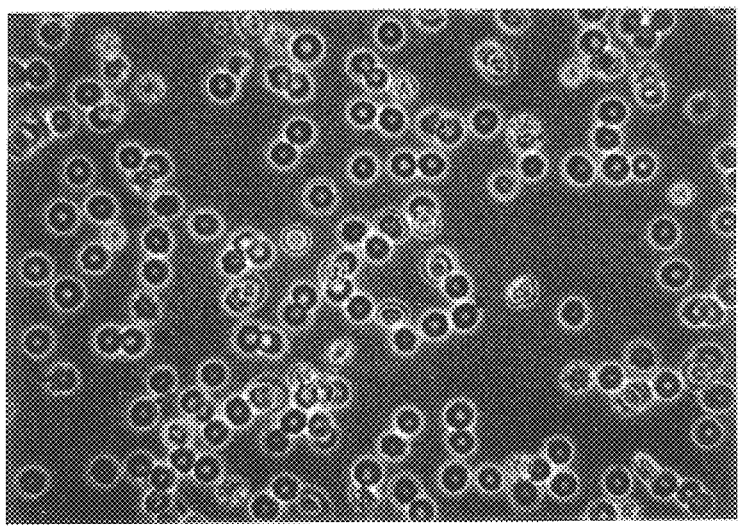
Figure 24C:
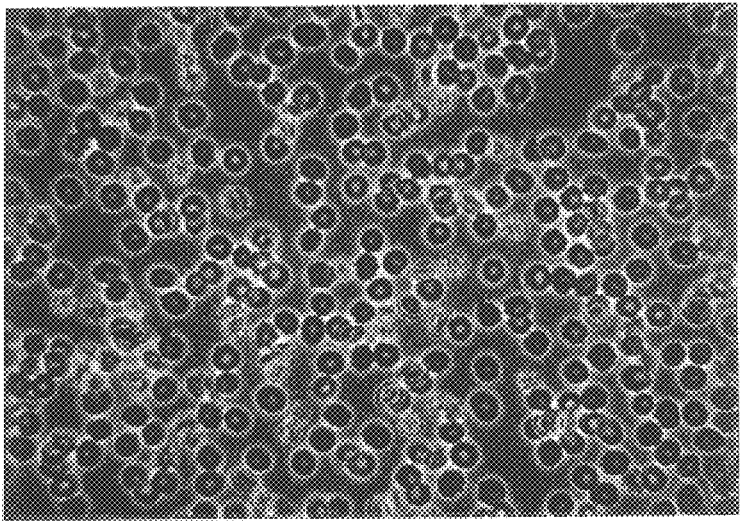
Figure 24D:
Figure 24E:
Figure 24F:
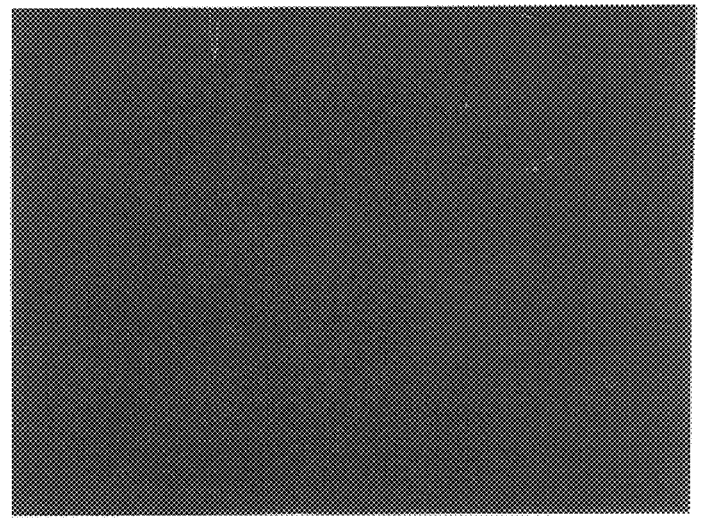

While fusion between cationic and anionic liposomes provides a good model system, fusion in vivo is somewhat different. The acceptor membrane is not composed solely of lipid, but contains a high concentration of proteins, many of which extend outward from the lipid bilayer and may interfere with fusion. Using erythrocyte ghosts as a representative membrane system, it was found that liposomes composed of DOPE:cholesterol:DODAC (40:45:15) fuse with cellular membranes (see, FIG. 21). In addition, it was found that fusion in this system, like those presented above, can also be inhibited using PEG-lipid conjugates. This results clearly establish the usefulness of these systems as programmable fusogenic carriers for intracellular drug delivery.

L. Programmed Fusion with Erythrocytes (RBCs)

LUVs composed of DOPE:cholesterol:DODAC (40:45:15) fused rapidly and extensively with RBCs (FIG. 22, panels a and b). Prolonged incubation caused extensive lysis of the RBCs and numerous fluorescently labeled "ghosts" were formed. Incorporation of PEG-ceramide (C8:0) at 5 mol % blocked fusion (FIG. 22, panels c and d) and this effect was maintained for up to 24 hr. This effect was somewhat surprising since the (C8:0) ceramide can exchange rapidly (i.e., within minutes) between liposomal membranes. It appears that either the RBCs cannot act as a sink for the PEG-ceramide, or there were insufficient RBCs to remove enough PEG-ceramide to allow fusion. However, when an exogenous sink for the PEG-ceramide was included, fusogenic activity was recovered within minutes (FIG. 22, panels e and f).

When PEG-ceramides with longer fatty amide chains (i.e., C14:0 or C20:0) were used, there was little fusion over 24 hr, even in the presence of an exogenous sink. This again was surprising as substantial fusion is observed over this time frame in liposomal systems when a sink is present. It was thought that some non-specific interaction between the sink (POPC/cholesterol) and the RBCs was occurring which hindered the ability of the POPC:cholesterol liposomes to absorb the PEG-ceramide. To overcome this, the fusogenic liposomes were pre-incubated with the sink before adding RBCS. FIG. 23 shows the results obtained under these conditions using PEG-ceramide (C14:0). No fusion was observed after pre-incubation of the fusogenic LUVs with the sink for 5 minutes prior to addition of RBCs (FIG. 23, panels a and b). However, after a 1 hr pre-incubation, some fusion with RBCs was observed (FIG. 23, panels c and d), suggesting that under these conditions the PEG-ceramide could transfer out of the liposomes and became fusogenic. With longer incubations (2 hr), the pattern of fluorescent labeling changed. Rather than diffuse labeling of the RBC plasma membranes, extensive punctate fluorescence was observed (FIG. 23, panels e and f) and this pattern was maintained for up to 24 hr. The punctate fluorescence did not appear to be associated with cells and it may represent fusion of fluorescent liposomes with the sink, although previous fluorescent measurements of liposome-liposome fusion indicated that this did not occur to any appreciable extent. A second possibility is that exchange of the fluorescent probe over the longer time courses leads to labeling of the sink, although it seems unlikely that this would prevent fusion and labeling of the RBCS. When PEG-ceramide (C20:0) was used, there was no evidence for fusion after preincubation of LUVs with the sink for 5 min (FIG. 24, panels a and b), 1 hr (FIG. 24, panels c and d), 2 hr (FIG. 24, panels e and f), or for up to 24 hr (results not shown).

FIGS. 22–24 unequivocally establish that the liposomes of the present invention exhibit programmable fusion with intact cells. Firstly, liposomes composed of DOPE:cholesterol:DODAC (40:45:15) that contain no PEG-lipid fuse rapidly and extensively with RBCs. Secondly, when the liposomes contain 5 mol % PEG-lipid fusion is blocked regardless of the composition of the lipid anchor. Thirdly, in the presence of a sink to which the PEG-lipid can transfer, fusogenic activity can be restored at a rate that is dependent on the nature of the lipid anchor. Although exchange leading to fusion could not be demonstrated when the PEG-ceramide (C20:0) was used, it is believed this is a problem with the assay rather than a lack of fusogenic potential. In vivo there would be an almost infinite sink for PEG-lipid exchange.

The foregoing is offered for purposes of illustration. It will be readily apparent to those skilled in the art that the operating conditions, materials, procedural steps and other parameters of the methods and test devices described herein may be further modified or substituted in ways without departing from the spirit and scope of the invention.

What is claimed is:

1. A method for increasing the rate of exchange of a bilayer stabilizing component from a liposome formulation to improve multiple dosing, said method comprising:
   (a) producing a first liposome composition having a lipid, a bioactive agent and a first bilayer stabilizing component, wherein said first bilayer stabilizing component is DSPE-PEG$_{2000}$;
   (b) determining the rate of exchange of DSPE-PEG$_{2000}$ from said first liposome composition using a fluorescent lipid mixing assay; and
   (c) preparing a second liposome formulation nearly identical to said first liposome formulation having said lipid, said bioactive agent, but substituting DSPE-PEG$_{2000}$ from said first liposome composition with a second bilayer stabilizing component having a faster rate of exchanges wherein said second liposome composition results in improved dosing.

2. The method of claim 1, wherein said first and second liposome compositions further comprise cholesterol.

3. The method of claim 1, wherein said lipid is a cationic lipid.

4. The method of claim 3, wherein said cationic lipid is a member selected from the group consisting of 3β-(N-(N', N'-dimethylaminoethane)carbamoyl)cholesterol, N,N-distearyl-N,N-dimethylammonium bromide, N-(1,2-dimyristyloxyprop-3-yl)-N,N-dimethyl-N-hydroxyethyl ammonium bromide, N,N-dioleyl-N,N-dimethylammonium chloride, diheptadecylamidoglycyl spermidine, N-(1-(2,3-dioleyloxy)propyl)-N-(2-(sperminecarboxamido)ethyl)-N, N-dimethylammonium trifluoroacetate, N-(1-(2,3-dioleoyloxy)propyl)-N,N,N-trimethylammonium chloride, N-(1-(2,3dioleyloxy)propyl)-N,N,N-trimethylammonium chloride and 1,2-bis(oleoyloxy)-3-dimethylaminopropane.

5. The method of claim 1, wherein said lipid is a member selected from the group consisting of dimyristoylphosphatidylethanolamine, dipalmitoylphosphatidylethanolamine, dioleoylphosphatidylethanolamine and distearoylphosphatidylethanolamine.

6. The method of claim 5, wherein said lipid is distearoylphosphatidylcholine.

7. The method of claim 1, wherein said second bilayer stabilizing component is polyethylene glycol conjugated to a lipid.

8. The method of claim 1, wherein said second bilayer stabilizing component is polyethylene glycol conjugated to a lipid which is a member selected from the group consisting of ceramides, phosphatidylethanolamines, phosphatidylcholines, sphingomyelins and cholesterol.

9. The method of claim 8, wherein said second bilayer stabilizing component is a hydrophilic polymer conjugated to a ceramide having a carbon chain length between $C_8$ to $C_{16}$.

10. The method of claim 9, wherein said second bilayer stabilizing component is a hydrophilic polymer conjugated to a ceramide having a carbon chain length between $C_8$ to $C_{16}$, wherein said carbon chain has at least one site of unsaturation.

11. The method of claim 10, wherein said second bilayer stabilizing component is polyethylene glycol conjugated to a $C_{-14}$-ceramide lipid.

12. The method of claim 11, wherein said second bilayer stabilizing component is polyethylene glycol conjugated to a $C_{-14}$-ceramide lipid, said $C_{-14}$-ceramide lipid having at least one site of unsaturation.

13. The method of claim 1, wherein said bioactive agent is a member selected from the group consisting of drugs, peptides, proteins, DNA and RNA.

14. The method of claim 1, wherein said faster rate of exchange varies from minutes to hours.

15. The method of claim 14, wherein said exchange rate is less than 4 hours.

16. The method of claim 14, wherein said exchange rate is less than about 1 hour.

17. The method of claim 1, wherein said lipid compositions further comprise cholesterol and a second lipid.

18. The method of claim 17, wherein said second lipid is a cationic lipid.

19. The method of claim 18, where said cationic lipid is a member selected from the group consisting of 3β-(N-(N',N'-dimethylaminoethane)carbamoyl)cholesterol, N,N-distearyl-N,N-dimethylammonium bromide, N-(1,2-dimyristyloxyprop-3-yl)-N,N-dimethyl-N-hydroxyethyl ammonium bromide, N,N-dioleyl-N,N-dimethylammonium chloride, diheptadecylamidoglycyl spermidine, N-(1-(2,3-dioleyloxy)propyl)-N-(2-(sperminecarboxamido)ethyl)-N,N-dimethylammonium trifluoroacetate, N-(1-(2,3-dioleoyloxy)propyl)-N,N,N-trimethylammonium chloride, N-(1-(2,3-dioleyloxy)propyl)-N,N,N-trimethylammonium chloride and 1,2-bis(oleoyloxy)-3 dimethylaminopropane.

20. The method of claim 1, wherein said second liposome composition comprises a lipid which is distearoylphosphatidylcholine, a second lipid which is 1,2-bis(oleoyloxy)-3-dimethylaminopropane, said bioactive agent is a nucleic acid, and said bilayer stabilizing component is a polyethylene glycol conjugated to a $C_{-14}$ ceramide lipid.

21. The method of claim 1, wherein said fluorescent lipid mixing assay is determined by the equation:

$$\% \text{ Fusion} = \frac{\frac{(F_{(t)} - L_{(t)})}{(F_T - L_T)} - \frac{(F_O - L_O)}{(F_T - L_T)}}{\frac{(M_{(t)} - L_{(t)})}{(M_T - L_T)} - \frac{(F_O - L_O)}{(F_T - L_T)}} \times 100$$

wherein: % fusion rate is relative to the % bilayer stabilizing component exchange rate, $F_{(t)}$ is fluorescence intensity at time t of said liposome composition;

$F_O$ is fluorescence intensity at zero time of said liposome composition;

$F_T$ is fluorescence intensity in the presence of a detergent of said liposome composition;

$M_{(t)}$ is fluorescence intensity at time t for a fused control;

$M_T$ is fluorescence intensity in the presence of a detergent of said fused control;

$L_O$ is fluorescence intensity at zero time of a light scattering control;

$L_T$ is fluorescence intensity in the presence of a detergent of said light scattering control; and $L_{(t)}$ is fluorescence intensity at time t for said light scattering control.

\* \* \* \* \*